(12) United States Patent
Wilson et al.

(10) Patent No.: US 10,137,176 B2
(45) Date of Patent: Nov. 27, 2018

(54) COMPOSITIONS AND METHODS FOR TREATING MPSI

(71) Applicant: The Trustees of the University of Pennsylvania, Philadelphia, PA (US)

(72) Inventors: James M. Wilson, Philadelphia, PA (US); Brittney L. Gurda, Collegeville, PA (US)

(73) Assignee: The Trustee of the University of Pennsylvania, Philadelphia, PA (US)

( * ) Notice: Subject to any disclaimer, the term of this patent is extended or adjusted under 35 U.S.C. 154(b) by 105 days.

(21) Appl. No.: 14/769,596

(22) PCT Filed: Mar. 13, 2014

(86) PCT No.: PCT/US2014/025509
§ 371 (c)(1),
(2) Date: Aug. 21, 2015

(87) PCT Pub. No.: WO2014/151341
PCT Pub. Date: Sep. 25, 2014

(65) Prior Publication Data
US 2016/0000887 A1 Jan. 7, 2016

Related U.S. Application Data

(60) Provisional application No. 61/788,724, filed on Mar. 15, 2013.

(51) Int. Cl.
| | | |
|---|---|---|
| *A61K 38/47* | (2006.01) | |
| *A61K 35/76* | (2015.01) | |
| *C12N 9/24* | (2006.01) | |
| *A61K 48/00* | (2006.01) | |
| *A61K 9/00* | (2006.01) | |
| *C12N 7/00* | (2006.01) | |

(52) U.S. Cl.
CPC ............ *A61K 38/47* (2013.01); *A61K 9/0019* (2013.01); *A61K 35/76* (2013.01); *A61K 48/0058* (2013.01); *C12N 7/00* (2013.01); *C12N 9/2402* (2013.01); *C12N 2750/14143* (2013.01); *C12Y 302/01076* (2013.01)

(58) Field of Classification Search
CPC .................................. A61K 38/47; C12N 7/00
See application file for complete search history.

(56) References Cited

U.S. PATENT DOCUMENTS

| | | | |
|---|---|---|---|
| 5,478,745 A | 12/1995 | Samulski et al. | |
| 6,149,909 A * | 11/2000 | Scott ................ | C12Y 302/0107 424/94.61 |
| 6,426,208 B1 | 7/2002 | Kakkis et al. | |
| 7,282,199 B2 * | 10/2007 | Gao ..................... | C07K 14/005 424/93.1 |
| 7,790,449 B2 | 9/2010 | Gao et al. | |
| 7,906,111 B2 | 3/2011 | Wilson et al. | |
| 8,318,480 B2 | 11/2012 | Gao et al. | |
| 9,827,295 B2 | 11/2017 | McIvor et al. | |
| 2005/0057114 A1 | 3/2005 | Calico | |
| 2006/0057114 A1 | 3/2006 | Whitley et al. | |
| 2007/0036760 A1 | 2/2007 | Wilson et al. | |
| 2009/0062144 A1 | 3/2009 | Guo | |
| 2013/0225666 A1 | 8/2013 | Kaspar et al. | |
| 2014/0017212 A1† | 1/2014 | Rebar | |
| 2016/0120960 A1 | 5/2016 | McIvor et al. | |
| 2018/0036388 A1 | 2/2018 | McIvor et al. | |

FOREIGN PATENT DOCUMENTS

| | | |
|---|---|---|
| CN | 102869779 A | 1/2013 |
| CN | 2014800109873 | 1/2018 |
| EP | 14770186.6 | 8/2016 |
| JP | 2002/514429 | 5/2002 |
| JP | 2016-501864 | 1/2018 |
| RU | 2196988 C2 | 5/2002 |
| RU2015144234/10(068118) | | 9/2017 |
| RU2015144234/10(068118) | | 2/2018 |
| WO | WO-1998/010088 | 3/1998 |
| WO | WO-1999/058691 | 11/1999 |
| WO | WO-2011/126808 | 10/2011 |
| WO | WO-2011/154520 | 12/2011 |
| WO | PCT/US14/25509 | 7/2014 |
| WO | WO-2014/186579 A1 | 11/2014 |
| WO | WO-2017/136500 A1 | 8/2017 |

OTHER PUBLICATIONS

Mizushima et al. (Nucleic Acids Res. Sep. 11, 1990;18(17):5322.).*
Mizushima et al. (Nucleic Acids Res. Sep. 11, 1990 ;18(17):5322). (Year: 1990).*
Jani et al. (Journal of Virological Methods. 1997; 64: 111-124) (Year: 1997).*
Yan et al. (Gene. 2012; 506: 289-294). (Year: 2012).*
Cotugno et al., Impact of Age at Administration, Lysosomal Storage, and Transgene Regulatory Elements on AAV2/8-Mediated Rat Liver Transduction, PLoS One, vol. 7(3):e33286, Mar. 13, 2012.
Ciron et al., Human alpha-Iduronidase Gene Transfer Mediated by Adeno-Associated Virus Types, 1, 2, and 5 in the Brain of Nonhuman Primates: Vector Diffusion and Biodistribution, Human Gene Therapy, vol. 20:350-360, Apr. 2009.

(Continued)

*Primary Examiner* — Scott Long

(74) *Attorney, Agent, or Firm* — Howson and Howson LLP

(57) ABSTRACT

A vector having an expression cassette having a hIDUA gene having a sequence of SEQ ID NO: 1 or a sequence at least about 95% identical thereto which encodes a functional human alpha-L-iduronidase is provided. The vector may be production vector or a rAAV8. Also provided are compositions containing these vectors and methods of treating MPSI and the symptoms associated with Hurler, Hurle-Scheie and Scheie syndromes.

22 Claims, 5 Drawing Sheets

Specification includes a Sequence Listing.

(56) References Cited

OTHER PUBLICATIONS

Ponder et al., Immune response hinders therapy for lysosomal storage diseases, J. Clin Invest., vol. 118(8):2686-2689, Jul. 24, 2008.
Belur et al., AAV Vector-Mediated Iduronidase Gene Delivery in a Murine Model of Mucopolysaccharidosis Type I: Comparing Different Routes of Delivery to the CNS (Abstract from Poster Session), The American Society of Gene & Cell Therapy, May 17, 2013.
Watson et al., Intrathecal administration of AAV vectors for the treatment of lysosomal storage in the brains of MPS I mice, Gene Therapy, vol. 13:917-925, Feb. 16, 2006.
Small Business Innovation Research-Small Business Technology Transfer, AAV Mediated Gene Transfer to the CNS for MPS I (Award Information), Retrieved from SBIR/STTR web site at https://www.sbir.gov/sbirsearch/detail/391096, Jan. 1, 2012.
International Search Report, dated Jul. 25, 2014, issued on parent International Patent Application No. PCT/US14/25509.
Andersen et al. "Herpesvirus-mediated gene delivery into the rat brain: specificity and efficiency of the neuron-specific enolase promoter." Cell Mol Neurobiol. Oct. 1993;13(5):503-15. (Oct. 1993).
Arbuthnot et al. "In vitro and in vivo hepatoma cell-specific expression of a gene transferred with an adenoviral vector." Hum Gene Ther. Aug. 20, 1996;7(13):1503-14. (Aug. 1996).
Bertola et al. "IDUA mutational profiling of a cohort of 102 European patients with mucopolysaccharidosis type I: identification and characterization of 35 novel α-L-iduronidase (IDUA) alleles." Hum Mutat. Jun. 2011;32(6):E2189-210. doi: 10.1002/humu.21479. Epub Mar. 10, 2011.
Boshart et al. "A very strong enhancer is located upstream of an immediate early gene of human cytomegalovirus." Cell. Jun. 1985;41(2):521-30. (Jun. 1985).
Bremer et al. "A novel mucopolysaccharidosis type I associated splice site mutation and IDUA splice variants." Mol Genet Metab. Nov. 2011;104(3):289-94. doi: 10.1016/j.ymgme.2011.07.012. Epub Jul. 20, 2011.
Cardone et al. "Correction of Hunter syndrome in the MPSII mouse model by AAV2/8-mediated gene delivery." Hum Mol Genet. Apr. 1, 2006;15(7):1225-36. Epub Feb. 27, 2006.
Chen et al, "Glycoproteomics analysis of human liver tissue by combination of multiple enzyme digestion and hydrazide chemistry." J Proteome Res. Feb. 2009;8(2):651-61. doi: 10.1021/pr8008012. (Publication Date (Web): Jan. 21, 2009).
Chen et al. "Expression of rat bone sialoprotein promoter in transgenic mice." J Bone Miner Res. May 1996;11(5):654-64. (May 1996).
Devereux et al. "A comprehensive set of sequence analysis programs for the VAX." Nucleic Acids Res. Jan. 11, 1984;12(1 Pt 1):387-95. (Jan. 1984).
Fisher et al. "Transduction with recombinant adeno-associated virus for gene therapy is limited by leading-strand synthesis." J Virol. Jan. 1996;70(1):520-32. (Jan. 1996).
Gossen et al. "Tight control of gene expression in mammalian cells by tetracycline-responsive promoters." Proc Natl Acad Sci U S A. Jun. 15, 1992;89(12):5547-51. (Jun. 1992).
Gossen et al. "Transcriptional activation by tetracyclines in mammalian cells." Science. Jun. 23, 1995;268(5218):1766-9. (Jun. 1995).
Hall. "BioEdit: a user-friendly biological sequence alignment editor and analysis program for Windows 95/98/NT." Nucl. Acids. Symp. Ser. 41:95-98 (1999).
Hansal et al. "Cutting Edge: Induction of Antigen-Specific Hyporesponsiveness by Transplantation of Hemopoietic Cells Containing an MHC Class I Transgene Regulated by a Lymphocyte-Specific Promoter" J Immunol Aug. 1, 1998, 161 (3) 1063-1068 (Aug. 1998).
Hartung et al. "Correction of metabolic, craniofacial, and neurologic abnormalities in MPS I mice treated at birth with adeno-associated virus vector transducing the human alpha-L-iduronidase gene." Mol Ther. Jun. 2004;9(6):866-75. (Jun. 2004).
Harvey et al. "Inducible control of gene expression: prospects for gene therapy." Curr Opin Chem Biol. Aug. 1998;2(4):512-8. (Aug. 1998).
Hayashi et al. "Human thyroxine-binding globulin gene: complete sequence and transcriptional regulation." Mol Endocrinol. Aug. 1993;7(8):1049-60. (Aug. 1993).
Hinderer et al. "Neonatal Systemic AAV Induces Tolerance to CNS Gene Therapy in MPS I Dogs and Nonhuman Primates." Mol Ther. Aug. 2015;23(8):1298-1307. doi: 10.1038/mt.2015.99. Epub May 29, 2015.
Kakkis et al. "Enzyme replacement therapy in feline mucopolysaccharidosis I." Mol Genet Metab. Mar. 2001;72(3):199-208. (Mar. 2001).
Li et al. "Synthetic muscle promoters: activities exceeding naturally occurring regulatory sequences." Nat Biotechnol. Mar. 1999;17(3):241-5. (Mar. 1999).
Magari et al. "Pharmacologic control of a humanized gene therapy system implanted into nude mice." J Clin Invest. Dec. 1, 1997;100(11):2865-72. (Dec. 1997).
Menon et al. "Architecture of the canine IDUA gene and mutation underlying canine mucopolysaccharidosis I." Genomics. Nov. 1992;14(3):763-8. (Nov. 1992).
Merrifiedl. "Solid Phase Peptide Synthesis. I. The Synthesis of a Tetrapeptide" J. Am. Chem. Soc., 1963, 85 (14), pp. 2149-2154 (Jul. 1963).
Meyer et al. "Improving single injection CSF delivery of AAV9-mediated gene therapy for SMA: a dose-response study in mice and nonhuman primates." Mol Ther. Mar. 2015;23(3):477-87. doi: 10.1038/mt.2014.210. Epub Oct. 31, 2014.
Miyatake et al. "Transcriptional targeting of herpes simplex virus for cell-specific replication." J Virol. Jul. 1997;71(7):5124-32. (Jul. 1997).
No et al. "Ecdysone-inducible gene expression in mammalian cells and transgenic mice." Proc Natl Acad Sci U S A. Apr. 16, 1996;93(8):3346-51. (Apr. 1996).
Pearson et al. "Improved tools for biological sequence comparison." Proc Nail Acad Sci U S A. Apr. 1988;85(8):2444-8.(Apr. 1988).
Piccioli et al. "Neuroantibodies: ectopic expression of a recombinant antisubstance P antibody in the central nervous system of transgenic mice." Neuron. Aug. 1995;15(2):373-84. (Aug. 1995).
Piccioli et al. "Neuroantibodies: molecular cloning of a monoclonal antibody against substance P for expression in the central nervous system." Proc Natl Acad Sci USA. Jul. 1, 1991;88(13):5611-5. (Jul. 1991).
Lock et al. "Rapid, simple, and versatile manufacturing of recombinant adeno-associated viral vectors at scale." Hum Gene Ther. Oct. 2010;21(10):1259-71. doi: 10.1089/hum.2010.055. (Published online Sep. 24, 2010.).
Sandig et al. "HBV-derived promoters direct liver-specific expression of an adenovirally transduced LDL receptor gene." Gene Ther. Nov. 1996;3(11):1002-9. (Nov. 1996).
Scott et al. "PCR detection of two RFLPs in exon I of the alpha-L-iduronidase (IDUA) gene." Hum Genet. Nov. 1992;90(3):327. (Nov. 1992).
Scott et al. "Structure and sequence of the human alpha-L-iduronidase gene." Genomics. Aug. 1991;13(4):1311-3. (Aug. 1992).
Scott et al. "Multiple polymorphisms within the alpha-L-iduronidase gene (IDUA): implications for a role in modification of MPS-I disease phenotype." Hum Mol Genet. Sep. 1993;2(9):1471-3. (Sep. 1993).
Scott et al. "Human alpha-L-iduronidase: cDNA isolation and expression." Proc Natl Acad Sci U S A. Nov. 1, 1991;88(21):9695-9. (Nov. 1991).
Stein et al. "The osteocalcin gene: a model for multiple parameters of skeletal-specific transcriptional control." Mol Biol Rep. Aug. 1997;24(3):185-96. (Aug. 1997).
Teng et al. "Identification and characterization of -3c-g acceptor splice site mutation in human alpha-L-iduronidase associated with mucopolysaccharidosis type IH/S." Clin Genet. Feb. 2000;57(2):131-6. (First published: Feb. 2000).
Wang et al. "Positive and negative regulation of gene expression in eukaryotic cells with an inducible transcriptional regulator." Gene Ther. May 1997;4(5):432-41. (May 1997).

(56) References Cited

OTHER PUBLICATIONS

Wang et al. "Ligand-inducible and liver-specific target gene expression in transgenic mice." Nat Biotechnol. Mar. 1997;15(3):239-43. (Mar. 1997).

Wolf et al. "Direct gene transfer to the CNS prevents emergence of neurologic disease in a murine model of mucopolysaccharidosis type I." Neurobiol Dis. Jul. 2011;43(1):123-33. doi: 10.1016/j.nbd.2011.02.015. Epub Mar. 17, 2011.

Wright, "Manufacturing and characterizing AAV-based vectors for use in clinical studies." Gene Ther. Jun. 2008;15(11):840-8. doi: 10.1038/gt.2008.65. Epub Apr. 17, 2005.

Yogalingam et al. "Identification and molecular characterization of alpha-L-iduronidase mutations present in mucopolysaccharidosis type I patients undergoing enzyme replacement therapy." Hum Mutat. Sep. 2004;24(3):199-207. First published: Jul. 26, 2004).

First Office Action issued on corresponding Russian Patent Application No. 2015144234 dated Sep. 14, 2017 with English translation.

Extended European search report issued on corresponding European Patent Application No. 14770186.6, dated Aug. 5, 2016.

Communication pursuant to Rule 70(2) and 70a (2) EPC issued on corresponding European Patent Application No. 14770186.6, dated Aug. 23, 2016.

Reply to communication pursuant to Rule 70(2) and 70a (2) EPC of Aug. 23, 2016issued on corresponding European Patent Application No. 14770186.6, filed Feb. 20, 2017.

International Search Report and Written Opinion issued on International Patent Application No. PCT/US17/16133, dated Apr. 5, 2017.

Cotugno, PLoS One, Impact of Age at Administration, Lysosomal Storage, and Transgene Regulatory Elements on AAV2/8-Mediated Rat Liver Transduction., vol. 7(3):E33286, Mar. 13, 2012.

Ciron, Human Gene Therapy, Human alpha-Iduronidase Gene Transfer Mediated by Adeno-Associated Virus Types 1, 2, and 5 in the Brain of Nonhuman Primates: Vector Diffusion and Biodistribution., vol. 1 20:350-360, Apr. 2009.

"*Homo sapiens* iduronidase, alpha-L-(IDUA), mRNA," Web page <https://www.ncbi.nlm.nih.gov/nuccore/110611238?sat=17&satkey=23266850>, 4 pages, Feb. 17, 2013, retrieved on Mar. 8, 2018, NCBI Reference Sequence NM_000203.3.

First Office Action issued in corresponding Japanese Patent Application No. 2016-501864 dated Jan. 31, 2018 with English translation.

"Alpha-L-iduronidase precursor [*Homo sapiens*]," Web page <https://www.ncbi.nlm.nih.gov/protein/110611239?sat=17&satkey=23266850>, 3 pages, Feb. 17, 2013, retrieved on Mar. 3, 2018, NCBI Reference Sequence_NP 000194.2.

"Alpha-L-iduronidase precursor [*Homo sapiens*]," Web page <https://www.ncbi.nlm.nih.gov/protein/110611239?sat=17&satkey=19459260>, 3 pages, Oct. 27, 2012, retrieved on Mar. 3, 2018, NCBI Reference Sequence NP_000194.2.

Chkioua L et al. Mucopolysaccharidosis type I: molecular characteristics of two novel alpha-L-iduronidase mutations in Tunisian patients. Diagn Pathol. Jun. 2011 3;6:47. doi: 10.1186/1746-1596-6-47. Published online Jun. 3, 2011.

Chkioua L et al. Molecular analysis of mucopolysaccharidosis type I in Tunisia: identification of novel mutation and eight Novel polymorphisms. Diagn Pathol. Apr. 26, 2011;6:39. doi: 10.1186/1746-1596-6-39. Published online Apr. 26, 2011.

Ashton LJ et al. Immunoquantification and enzyme kinetics of alpha-L-iduronidase in cultured fibroblasts from normal controls and mucopolysaccharidosis type I patients. Am J Hum Genet. Apr. 1992;50(4):787-94. (Apr. 1992).

Scott HS et al. alpha-L-iduronidase mutations (Q70X and P533R) associate with a severe Hurler phenotype. Hum Mutat. 1992;1(4):333-9.

MacDonald ME et al. Huntington disease-linked locus D4S111 exposed as the alpha-L-iduronidase gene. Somat Cell Mol Genet. Jul. 1991;17(4):421-5.

Scott HS et al. Chromosomal localization of the human alpha-L-iduronidase gene (IDUA) to 4p16.3. Am J Hum Genet. Nov. 1990;47(5):802-7.

Second Office Action issued in corresponding Russian Patent Application No. 2015144234 dated Feb. 12, 2018 with English translation.

First Office Action issued in corresponding Chinese Patent Application No. 201480010987.3 dated Jan. 22, 2018.

\* cited by examiner
† cited by third party

FIG. 1A

```
pENN.AAV.TBG.PI.        6863 bp     DNA     circular

FEATURES             Location/Qualifiers
    misc_structure   complement(5566..6381)
                     /vntifkey="88"
                     /label=Kan-r
    rep_origin       4249..4891
                     /vntifkey="33"
                     /label=pUC\origin\of\replication
    promoter         442..901
                     /vntifkey="29"
                     /label=TBG
    TATA_signal      885..888
                     /vntifkey="41"
                     /label=TATA
    enhancer         221..320
                     /vntifkey="9"
                     /label=Alpha\mic/bik
    enhancer         327..426
                     /vntifkey="9"
                     /label=Alpha\mic/bik
    intron           1027..1159
                     /vntifkey="15"
                     /label=Intron_1
                     /note="chimeric intron"
    polyA_signal     3261..3387
                     /vntifkey="25"
                     /label=Rabbit\globin\poly\A
    repeat_region    1..130
                     /vntifkey="34"
                     /label=5'\ITR
    repeat_region    complement(3476..3605)
                     /vntifkey="34"
                     /label=3'\ITR
    rep_origin       complement(3782..4220)
                     /vntifkey="33"
                     /label=f1\ori
    CDS              1251..3212
                     /vntifkey="4"
                     /label=Human\alpha-L-IDUA
```

FIG. 1B

```
BASE COUNT     1584 a      1971 c      1702 g      1606 t
ORIGIN 1 ctgcgcgctc gctcgctcac tgaggccgcc cgggcaaagc ccgggcgtcg ggcgacctttt
  61 ggtcgcccgg cctcagtgag cgagcgagcg cgcagagagg gagtggccaa ctccatcact
 121 aggggttcct tgtagttaat gattaacccg ccatgctact tatctaccag ggtaatgggg
 181 atcctctaga actatagcta gaattcgccc ttaagctagc aggttaattt ttaaaaagca
 241 gtcaaaagtc caagtggccc ttggcagcat ttactctctc tgtttgctct ggttaataat
 301 ctcaggagca caaacattcc agatccaggt taattttaa aaagcagtca aaagtccaag
 361 tggcccttgg cagcatttac tctctctgtt tgctctggtt aataatctca ggagcacaaa
 421 cattccagat ccggcgcgcc agggctggaa gctaccttg acatcatttc ctctgcgaat
 481 gcatgtataa tttctacaga acctattaga aaggatcacc cagcctctgc ttttgtacaa
 541 ctttccctta aaaaactgcc aattccactg ctgtttggcc caatagtgag aactttttcc
 601 tgctgcctct tggtgctttt gcctatggcc cctattctgc ctgctgaaga cactcttgcc
 661 agcatggact taaacccctc cagctctgac aatcctcttt ctctttttgtt ttacatgaag
 721 ggtctggcag ccaaagcaat cactcaaagt tcaaaccttta tcattttttg ctttgttcct
 781 cttggccttg gttttgtaca tcagctttga aaataccatc ccaggttaa tgctggggtt
 841 aatttataac taagagtgct ctagttttgc aatacaggac atgctataaa aatggaaaga
 901 tgttgctttc tgagagacag ctttattgcg gtagtttatc acagttaaat tgctaacgca
 961 gtcagtgctt ctgacacaac agtctcgaac ttaagctgca gaagttggtc gtgaggcact
1021 gggcaggtaa gtatcaaggt tacaagacag gtttaaggag accaatagaa actgggcttg
1081 tcgagacaga gaagactctt gcgtttctga taggcaccta ttggtcttac tgacatccac
1141 tttgccttttc tctccacagg tgtccactcc cagttcaatt acagctctta aggctagagt
1201 acttaatacg actcactata ggctagcctc gagaattcac gcgtgccacc atgcggcccc
1261 tgaggcctag agctgctctg ctggcactgc tggccagtct gctggctgcc cctcctgtgg
1321 cccctgccga agcccctcac ctggtgcatg tggatgccgc cagagccctg tggcctctgc
1381 ggagattctg gcggagcacc ggcttttgcc ccccactgcc tcacagccag gccgaccagt
1441 acgtgctgag ctgggaccag cagctgaacc tggcctacgt gggcgccgtg ccccacagag
1501 gcatcaaaca ggtgagaacc cactggctgc tggaactggt gacaacccgg ggctccaccg
1561 gcagaggcct gagctacaac ttcacccacc tggacggcta cctggacctg ctgagagaga
1621 accagctgct gcccggcttc gagctgatgg gcagcgccag cggccacttc accgacttcg
1681 aggacaagca gcaagtcttt gagtggaagg acctggtgtc cagcctggcc agacggtaca
1741 tcggcagata cggactggcc cacgtgtcca agtggaactt cgagacatgg aacgagcccg
1801 accaccacga cttcgacaac gtgtcaatga ccatgcaggg ctttctgaac tactacgacg
1861 cctgctccga gggcctgaga ccgccagtc ctgccctgag actgggcgga cccggcgata
1921 gcttccacac ccccccaga agccccctga gctggggcct gctgagacac tgccacgacg
1981 gcaccaattt cttcaccggc gaggccggcg tcggctgga ctacatcagc ctgcaccgga
2041 agggcgccag aagcagcatc agcatcctgg aacaggaaaa ggtcgtcgcc cagcagatcc
2101 ggcagctgtt ccccaagttc gccgacaccc catctacaa cgacgaggcc gaccccctgg
2161 tgggatggtc actgcctcag ccttggagag ccgacgtgac ctacgccgct atggtggtga
2221 aagtgatcgc ccagcatcag aacctgctgc tggccaacac caccagcgcc ttcccttacg
2281 ccctgctgag caacgacaac gccttcctga gctaccaccc caccccttc gcccagagaa
2341 ccctgaccgc ccggttccag gtgaacaaca ccagaccccc ccacgtgcag ctgctgagaa
2401 agcccgtgct gaccgctatg gactgctggc tctgctgga cgaggaacag ctgtgggccg
2461 aagtgtccca ggccggcacc gtgctggaca gcaatcatac agtgggcgtg ctggcctccg
2521 cccacagacc tcaggaccc gccgatgctt ggcgggctgc cgtgctgatc tacgccagcg
2581 acgataccag agcccacccc aacagatccg tggccgtgac cctgcggctg agaggcgtgc
2641 caccaggccc tggactggtg tacgtgacca gatacctgga caacggcctg tgcagccccg
2701 acggcgaatg gcgcagactg ggcagacctg tgttccccac cgccgagcag ttccggcgga
2761 tgagagccgc tgaggatcct gtggctgctg cccctagacc tctgcctgct ggcggcagac
```

FIG. 1C

```
2821 tgaccctgag gcccgctctg agactgccta gtctgctgct ggtgcacgtg tgcgccaggc
2881 ccgagaagcc tcccggccag gtgacaagac tgagagccct gcccctgacc cagggccagc
2941 tggtgctggt gtggtccgat gagcacgtgg gcagcaagtg cctgtggacc tacgagatcc
3001 agttcagcca ggacggcaag gcctacaccc ccgtgtcccg gaagcccagc accttcaacc
3061 tgttcgtgtt cagccccgat acaggcgccg tgtccggctc ttatagagtg cgggccctgg
3121 actactgggc cagacccggc cctttcagcg accccgtgcc ctacctggaa gtgcccgtgc
3181 ctagaggccc ccctagcccc ggcaacccct tgagtcgacc gggcggcctc gaggacgggg
3241 tgaactacgc ctgaggatcc gatcttttc cctctgccaa aaattatggg gacatcatga
3301 agcccttga gcatctgact tctggctaat aaaggaaatt tatttcatt gcaatagtgt
3361 gttggaattt tttgtgtctc tcactcggaa gcaattcgtt gatctgaatt tcgaccaccc
3421 ataatacca ttaccctggt agataagtag catggcgggt taatcattaa ctacaaggaa
3481 cccctagtga tggagttggc cactccctct ctgcgcgctc gctcgctcac tgaggccggg
3541 cgaccaaagg tcgcccgacg cccgggcttt gcccgggcgg cctcagtgag cgagcgagcg
3601 cgcagcctta attaacctaa ttcactggcc gtcgtttac aacgtcgtga ctgggaaaac
3661 cctggcgtta cccaacttaa tcgccttgca gcacatcccc ctttcgccag ctggcgtaat
3721 agcgaagagg cccgcaccga tcgcccttcc caacagttgc gcagcctgaa tggcgaatgg
3781 gacgcgccct gtagcggcgc attaagcgcg gcgggtgtgg tggttacgcg cagcgtgacc
3841 gctacacttg ccagcgccct agcgcccgct cctttcgctt tcttcccttc ctttctcgcc
3901 acgttcgccg gctttccccg tcaagctcta atcggggc tcccttagg gttccgattt
3961 agtgctttac ggcacctcga ccccaaaaaa cttgattagg gtgatggttc acgtagtggg
4021 ccatcgccct gatagacggt ttttcgccct ttgacgttgg agtccacgtt ctttaatagt
4081 ggactcttgt tccaaactgg aacaacactc aaccctatct cggtctattc ttttgattta
4141 taagggattt tgccgatttc ggcctattgg ttaaaaaatg agctgattta acaaaaattt
4201 aacgcgaatt ttaacaaaat catgtgagca aaaggccagc aaaaggccag gaaccgtaaa
4261 aaggccgcgt tgctggcgtt tttccatagg ctccgccccc ctgacgagca tcacaaaaat
4321 cgacgctcaa gtcagaggtg gcgaaacccg acaggactat aaagatacca ggcgtttccc
4381 cctggaagct ccctcgtgcg ctctcctgtt ccgaccctgc cgcttaccgg atacctgtcc
4441 gcctttctcc cttcgggaag cgtggcgctt tctcatagct cacgctgtag gtatctcagt
4501 tcggtgtagg tcgttcgctc caagctgggc tgtgtgcacg aacccccgt tcagcccgac
4561 cgctgcgcct tatccggtaa ctatcgtctt gagtccaacc cggtaagaca cgacttatcg
4621 ccactggcag cagccactgg taacaggatt agcagagcga ggtatgtagg cggtgctaca
4681 gagttcttga agtggtggcc taactacggc tacactagaa gaacagtatt tggtatctgc
4741 gctctgctga agccagttac cttcggaaaa agagttggta gctcttgatc cggcaaacaa
4801 accaccgctg gtagcggtgg ttttttgtt tgcaagcagc agattacgcg cagaaaaaaa
4861 ggatctcaag aagatccttt gatcttttct acggggtctg acgctcagtg gaacgaaaac
4921 tcacgttaag ggattttggt catgagatta tcaaaaagga tcttcaccta gatccttttg
4981 atcctccggc gttcagcctg tgccacagcc gacaggatgg tgaccaccat tgccccata
5041 tcaccgtcgg tactgatccc gtcgtcaata aaccgaaccg ctacaccctg agcatcaaac
5101 tcttttatca gttggatcat gtcggcggtg tcgcggccaa gacggtcgag cttcttcacc
5161 agaatgacat caccttcctc caccttcatc ctcagcaaat ccagcccttc ccgatctgtt
5221 gaactgccgg atgccttgtc ggtaaagatg cggttagctt ttacccctgc atctttgagc
5281 gctgaggtct gcctcgtgaa gaaggtgttg ctgactcata ccaggcctga atcgccccat
5341 catccagcca gaaagtgagg gagccacggt tgatgagagc tttgttgtag gtggaccagt
5401 tggtgatttt gaacttttgc tttgccacgg aacggtctgc gttgtcggga agatgcgtga
5461 tctgatcctt caactcagca aaagttcgat ttattcaaca agccgccgt cccgtcaagt
5521 cagcgtaatg ctctgccagt gttacaacca attaaccaat tctgattaga aaaactcatc
5581 gagcatcaaa tgaaactgca atttattcat atcaggatta tcaataccat attttttgaaa
5641 aagccgtttc tgtaatgaag gagaaaactc accgaggcag ttccatagga tggcaagatc
```

FIG. 1D

```
5701  ctggtatcgg tctgcgattc cgactcgtcc aacatcaata caacctatta atttcccctc
5761  gtcaaaaata aggttatcaa gtgagaaatc accatgagtg acgactgaat ccggtgagaa
5821  tggcaaaagc ttatgcattt ctttccagac ttgttcaaca ggccagccat tacgctcgtc
5881  atcaaaatca ctcgcatcaa ccaaaccgtt attcattcgt gattgcgcct gagcgagacg
5941  aaatacgcga tcgctgttaa aaggacaatt acaaacagga atcgaatgca accggcgcag
6001  gaacactgcc agcgcatcaa caatattttc acctgaatca ggatattctt ctaatacctg
6061  gaatgctgtt ttcccgggga tcgcagtggt gagtaaccat gcatcatcag gagtacggat
6121  aaaatgcttg atggtcggaa gaggcataaa ttccgtcagc cagtttagtc tgaccatctc
6181  atctgtaaca tcattggcaa cgctaccttt gccatgtttc agaaacaact ctggcgcatc
6241  gggcttccca tacaatcgat agattgtcgc acctgattgc ccgacattat cgcgagccca
6301  tttataccca tataaatcag catccatgtt ggaatttaat cgcggcctcg agcaagacgt
6361  ttcccgttga atatggctca taacacccct tgtattactg tttatgtaag cagacagttt
6421  tattgttcat gatgatatat ttttatcttg tgcaatgtaa catcagagat tttgagacac
6481  catgttcttt cctgcgttat cccctgattc tgtggataac cgtattaccg cctttgagtg
6541  agctgatacc gctcgccgca gccgaacgac cgagcgcagc gagtcagtga gcgaggaagc
6601  ggaagagcgc ccaatacgca aaccgcctct ccccgcgcgt tggccgattc attaatgcag
6661  ctggcacgac aggtttcccg actggaaagc gggcagtgag cgcaacgcaa ttaatgtgag
6721  ttagctcact cattaggcac cccaggcttt acactttatg cttccggctc gtatgttgtg
6781  tggaattgtg agcggataac aatttcacac aggaaacagc tatgaccatg attacgccag
6841  atttaattaa ggccttaatt agg
```

COMPOSITIONS AND METHODS FOR TREATING MPSI

CROSS-REFERENCE TO RELATED APPLICATIONS

This application is a 371 of PCT/US2014/025509, filed Mar. 13, 2014, which claims the benefit of the priority of U.S. Provisional Patent Application No. 61/788,724, filed Mar. 15, 2013. These priority applications are hereby incorporated by reference herein.

BACKGROUND OF THE INVENTION

The mucopolysaccharidoses are a group of inherited disorders caused by a lack of specific lysosomal enzymes involved in the degradation of glycosaminoglycans (GAG), also called mucopolysaccharides. The accumulation of partially-degraded GAG causes interference with cell, tissue, and organ function. Over time, the GAG accumulates within cells, blood, and connective tissue, resulting in increasing cellular and organ damage. The most serious of the mucopolysaccharidosis (MPS) disorders, MPS I, is caused by a deficiency of the enzyme α-L-iduronidase (IDUA). This leads to three clinical syndromes which in order of severity are Hurler, Hurler-Scheie and Scheie syndromes. Each is inherited in an autosomal recessive manner with the extent of enzyme deficiency being directly related to the severity of the clinical phenotype.

The IDUA gene has been reported to provide instructions for producing an enzyme called alpha-L-iduronidase, which is essential for the breakdown of large sugar molecules called glycosaminoglycans (GAGs). Specifically, alpha-L-iduronidase is reported to remove sulfate from a molecule known as sulfated alpha-L-iduronic acid, which is present in two GAGs called heparan sulfate and dermatan sulfate. Alpha-L-iduronidase is located in lysosomes, compartments within cells that digest and recycle different types of molecules. More than 100 mutations in the IDUA gene have been found to cause mucopolysaccharidosis type I (MPS I). Mutations that change one DNA building block (nucleotide) are the most common. Mutations that cause MPS I to reduce or completely eliminate the function of alpha-L-iduronidase.

With respect to the clinical syndromes, the current standard of care for Hurler syndrome is hematopoietic stem cell transplantation (HSCT) such as bone marrow transplantation (BMT) or umbilical cord blood transplantations (UCBT). The procedure is done as early as possible, and before the age of two, to impact on both somatic and CNS aspects of the disease. However, HSCT for MPS I remains associated with a significant amount of morbidity and a 20% mortality rate. If transplantation is not an option, then enzyme replacement therapy (ERT) may be started which requires a weekly infusion of enzyme for the life of the patient. ERT does not impact on the progression of CNS disease but does partially improve the somatic manifestations. Organomegaly is significantly improved although aspects of the disease in the skeletal system, eye and heart are only partially improved. Patients may require surgery to stabilize the hip and knee and to treat carpal tunnel syndrome and finger contractions. Cardiac disease is treated medically although surgery may eventually be required.

ERT for MPS I provides exogenous enzyme for uptake into lysosomes and increased catabolism of GAG. Although the lysosomal enzymes function internally, cell-surface mannose-6-phosphate receptors are capable of binding, internalizing, and delivering these enzymes to the lysosomes. Recombinant IDUA (Aldurazyme®, BioMarin) is approved by FDA for patients with Hurler and Hurler-Scheie forms of MPS I and for patients with the Scheie form who have moderate to severe symptoms and was shown to improve pulmonary function and walking capacity. ERT has also been observed to reduce hepatomegaly in MPS I patients, as well as the levels of urinary GAG. However, because intravenous enzyme does not easily cross into the brain, ERT does not currently address the neurological symptoms experienced by some MPS I patients.

Complications of ERT revolve around immune response to the recombinant enzyme which can range from mild to full-blown anaphylaxis as well as complications of life-long peripheral access such as local and systemic infections. Up to 91% of patients receiving Aldurazyme develop antibodies to the enzyme, although it is not clear how much it affects efficacy. Furthermore, ERT requires weekly intravenous (i.v.) infusions, administered over a period of 3-8 hours in a hospital setting, which significantly impacts patient quality of life and, at a high expense, is a major strain on health care reimbursement systems.

In light of these limitations, a treatment that can more effectively correct the morbidity associated with MPS I remains an unmet medical need.

SUMMARY OF THE INVENTION

In one aspect, the invention provides an expression cassette comprising a human alpha-L-iduronidase (hIDUA) gene having the nucleotide sequence of SEQ ID NO: 1 or a sequence at least about 95% identical to SEQ ID NO: 1 which encodes a functional human alpha-L-iduronidase in human cells, wherein said expression cassette further comprises regulatory control sequences which direct expression of the human alpha-L-iduronidase in human cells, said regulatory control sequences comprising a liver-specific promoter.

In another aspect, the invention provides a vector containing the expression cassette. In one embodiment, the expression cassette is located on a cis plasmid. In another embodiment, the expression cassette is located on pENN.T-BG.hIDUA.nRBG.

In yet another aspect, the invention provides a recombinant adeno-associated virus (rAAV) particle having an AAV capsid and having packaged therein a left inverted terminal repeat (ITR), a human alpha-L-iduronidase (hIDUA) gene under the control of regulatory sequences which control expression thereof, and an AAV right ITR, wherein said hIDUA gene has a sequence shown in SEQ ID NO: 1 (FIG. 1) or a sequence at least about 95% identical thereto which encodes a functional human alpha-L-iduronidase. In one embodiment, the functional hIDUA gene is expressed under the control of a liver-specific promoter. Such a promoter may be a thyroxin binding globulin (TBG) promoter.

In a further aspect, the invention provides the recombinant adeno-associated viral particle AAV2/8.TBG.hIDUA.co.

In a yet another aspect, the invention provides a composition useful for treating mucopolysaccharidosis type I (MPS I) comprising the rAAV comprising the expression cassette described herein and a pharmaceutically acceptable carrier.

In still a further aspect, the invention provides a method for treating type I mucopolysaccharidosis comprising delivering an effective amount of a composition comprising a pharmaceutically acceptable carrier and a rAAV as described herein.

In yet another aspect, the invention provides a method for treating or ameliorating the symptoms of Hurler, Hurler-Scheie and/or Scheie syndromes.

Still other aspects and advantages of the invention will be apparent from the detailed description of the invention.

BRIEF DESCRIPTION OF THE FIGURES

FIGS. 1A-1D provides the sequence of the pENN.AAV.T-BG.PI.hIDUA.RGB plasmid [SEQ ID NO:3] described herein, which includes the nucleic acid sequence of the functional human IDUA gene. The gene of the functional IDUA located at position 1251-3213 of FIG. 1 and its encoded enzyme sequence are also provided in SEQ ID NO: 1 and 2. The sequence is further annotated to identify the sequences of the alpha mic/bik enhancers, the intron 1, the rabbit globulin poly A, the ITRs, the origin of replication.

DETAILED DESCRIPTION OF THE INVENTION

Figure 2:
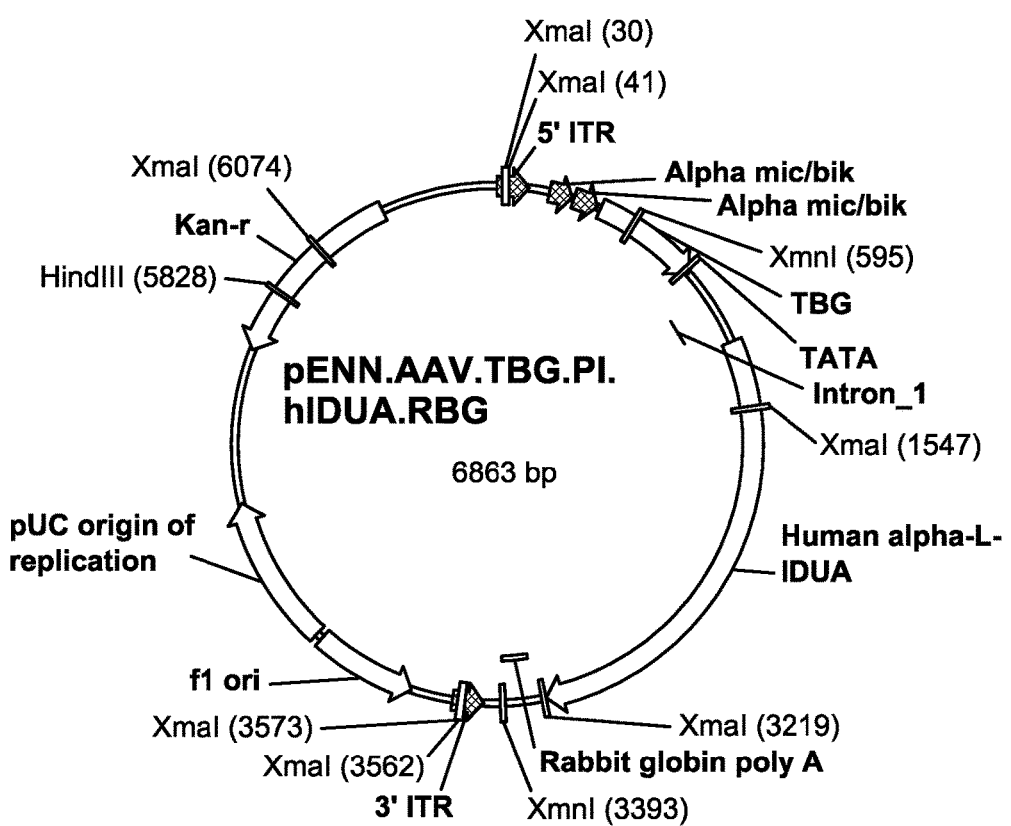
FIG. 2 provides the circular map of pENN.AAV.TBG.PI-.hIDUA.RGB.

The compositions described herein provide an expression cassette carrying a human IDUA gene which expresses a therapeutically effective amount of functional human alpha-L-iduronidase enzyme in a human subject.

As used herein, a "therapeutically effective amount" refers to the amount of the composition which delivers and expresses in the target cells an amount of enzyme sufficient to ameliorate or treat the symptoms of Hurler, Hurler-Scheie and/or Scheie syndromes, and or MPS I. "Treatment" may include preventing the worsening of the symptoms of one of the syndromes (or MPS I) and possibly reversal of one or more of the symptoms thereof.

As used herein a "functional human alpha-L-iduronidase" refers to a human alpha-L-iduronidase enzyme which functions normally in humans without MPS1 or an associated syndrome such as Hurler, Hurler-Scheie and/or Scheie syndromes. Conversely, a human alpha-L-iduronidase enzyme variant which causes MPS1 or one of these syndromes is considered non-functional. In one embodiment, a functional human alpha-1-iduronidase has the amino acid sequence of a wild-type human alpha-L-iduronidase described by Bremer et al, Mol. Genet. Metab. 104 (3): 289-294 (2011), NCBI Reference Sequence NP_000194.2, reproduced in SEQ ID NO:2 (653 amino acids). However, several naturally occurring functional polymorphisms (variants) of this sequence have been described and may be encompassed within the scope of this invention. These variants include, with reference to SEQ ID NO: 2, a N-linked glycosylation at position 110 [Chen et al, J Proteome Res., 8:651-661 (2009)], a change from H to Q at amino acid position 33 [SEQ ID NO: 7, VAR_003350; Scott, H S, et al, Proc Natl Acad. Sci, 88:9695-9699 (1991); Scott, H S, et al, Genomics, 12:1311-1313 (1992); Scott H S, et al, Hum Genet, 90:327-327 (1992); Bertola F., et al, Hum Mutat, 32: E2189-E2210 (2011)], an H to Q reduction at amino acid position 82 [SEQ ID NO: 8, VAR_020976; Scott, H S, Hum Genet, cited above], a change from R to Q at position 105 [SEQ ID NO: 9, VAR_003356; Scott, Hum Genet, cited above; Bertola et al, cited above], a change from G to Rat position 116 [SEQ ID NO: 12, VAR_003367], a change from V to A at position 279 [SEQ ID NO: 11, VAR_003359], a change from L to R at position 346 [SEQ ID NO: 12, VAR_017436, Teng, Y N, et al, Clin. Genet, 57: 131-136 (2000)], a change from A to T at position 361 [SEQ ID NO: 13, VAR_003364; Scott, H S, et al, Hum Mol Genet, 2: 1471-1473 (1993); Yogalingam et al, Hum Mutat, 24: 199-207 (2004); Bertola, et al, cited above], a change from H to N at position 449 [SEQ ID NO: 14, VAR_066228, Bertola et al, cited above], a change from V to I at position 454 [SEQ ID NO: 15, VAR_003372; Yogalingam et al, cited above; Bertola, et al, cited above], a change from A to T at position 591 [SEQ ID NO: 16, VAR_0066231, Bertola et al, cited above], and a change from A to T at position 622 [SEQ ID NO: 17, Scott et al, Genomics, cited above]. See, e.g., UniProtKB/Swiss-Prot; www.uniprot.org/uniprot/P35475. In another embodiment, a functional human alpha-L-iduronidase may include a synthetic amino acid sequence in which all or a portion of the first 26 amino acids of SEQ ID NO:2, which correspond to the leader (signal) peptide, are replaced with a heterologous leader peptide. This leader peptide, which is responsible for transporting the enzyme out of the cell through its secretory pathway into the circulation, may be substituted with another suitable leader peptide, e.g., such as the leader peptides from interleukin-2 (IL-2) or oncostatin. Suitable leader peptides are preferably, although not necessarily of human original. Suitable leader peptides may be chosen from http://proline.bic.nus.edu.sg/spdb/zhang270.htm, which is incorporated by reference herein, or may be determined using a variety of computational programs for determining the leader (signal) peptide in a selected protein. Although not limited, such sequences may be from about 15 to about 50 amino acids in length, or about 20 to about 28 amino acids in length, or may be larger or smaller as required. In addition, at least one in vitro assay has been described as being useful to assess the enzymatic activity of an IDUA enzyme [see, e.g., Kakkis et al, Mol Genet Metabol, 2001 March; 72(3): 199-208].

Suitably, the composition and method described herein do not require long term, repeated weekly injections of a therapeutic dose. Without wishing to be bound by theory, the method described herein is believed to be useful for correcting the central nervous system phenotype in addition to somatic symptoms associated with MPSI disorders.

Expression Cassette

The expression cassette is composed of, at a minimum, a gene and its regulatory sequences. Where the cassette is designed to be expressed from a recombinant adeno-associated virus, the expression cassette further contains 5' and 3' AAV inverted terminal repeats (ITRs). These ITR's may be full-length, or one or both of the ITRs may be truncated. For example, a truncated 5' ITR containing a deletion of the D sequence and a terminal resolution site (trs) deletion may be used, e.g., for a self-complementary AAV. In one embodiment, the rAAV is pseudotyped, i.e., the AAV capsid is from a different source AAV than that the AAV which provides the ITRs. In one embodiment, the ITRs of AAV serotype 2 are used. However, ITRs from other suitable sources may be selected.

As described herein, patients suffering from one of the conditions described herein are delivered an expression cassette which carries a functional human alpha-L-iduronidase (hIDUA) gene under control of regulatory sequences which direct expression of a functional human alpha-L-iduronidase enzyme in the cells.

The expression cassette contains a hIDUA gene characterized by having the nucleotide sequence of SEQ ID NO: 1. This sequence, developed by the inventors, has an identity of about 83% with the published gene sequence of Genbank NP000194.2 encoding SEQ ID NO: 2. In another embodiment, the expression cassette contains a hIDUA gene characterized by having the nucleotide sequence at least about 80% identical to SEQ ID NO: 1 and encodes a functional human alpha-L-iduronidase. In another embodiment, the sequence is at least about 85% identity to SEQ ID NO: 1 or at least about 90% identical to SEQ ID NO:1 and encodes a functional human alpha-L-iduronidase. In one embodiment, the sequence is at least about 95% identical to SEQ ID NO:1, at least about 97% identical to SEQ ID NO:1, or at least about 99% identical to SEQ ID NO: 1 and encodes a functional human alpha-L-iduronidase. In one embodiment, this encompasses full-length hIDUA gene, including the leader peptide sequences of the human alpha-L-iduronidase (i.e., encoding about amino acid 26, or about amino acid 27, to about amino acid 653 of SEQ ID NO:2), corresponding to about 1 to about 78 of SEQ ID NO:1. In another embodiment, the hIDUA gene encodes a functional synthetic human alpha-L-iduronidase enzyme which is synthetic peptide comprising a heterologous leader sequence fused to the secreted portion of a functional alpha-L-iduronidase enzyme, i.e., about amino acids 27 to about 653 of SEQ ID NO: 2 or one of the functional variants thereof which are identified herein.

Identity or similarity with respect to a sequence is defined herein as the percentage of amino acid residues in the candidate sequence that are identical (i.e., same residue) or similar (i.e., amino acid residue from the same group based on common side-chain properties, see below) with the peptide and polypeptide regions provided herein, after aligning the sequences and introducing gaps, if necessary, to achieve the maximum percent sequence identity. Percent (%) identity is a measure of the relationship between two polynucleotides or two polypeptides, as determined by comparing their nucleotide or amino acid sequences, respectively. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology. There are a number of algorithms, and computer programs based thereon, which are available to be used the literature and/or publically or commercially available for performing alignments and percent identity. The selection of the algorithm or program is not a limitation of the present invention.

Examples of suitable alignment programs including, e.g., the software CLUSTALW under Unix and then be imported into the Bioedit program (Hall, T. A. 1999, BioEdit: a user-friendly biological sequence alignment editor and analysis program for Windows 95/98/NT. Nucl. Acids. Symp. Ser. 41:95-98); the Wisconsin Sequence Analysis Package, version 9.1 (Devereux J. et al., Nucleic Acids Res., 12:387-395, 1984, available from Genetics Computer Group, Madison, Wis., USA). The programs BESTFIT and GAP, may be used to determine the % identity between two polynucleotides and the % identity between two polypeptide sequences.

Other programs for determining identity and/or similarity between sequences include, e.g., the BLAST family of programs available from the National Center for Biotechnology Information (NCB), Bethesda, Md., USA and accessible through the home page of the NCBI at www.ncbi.nlm.nih.gov), the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used; and FASTA (Pearson W. R. and Lipman D. J., Proc. Natl. Acad. Sci. USA, 85:2444-2448, 1988, available as part of the Wisconsin Sequence Analysis Package). SeqWeb Software (a web-based interface to the GCG Wisconsin Package: Gap program).

As used throughout this specification and the claims, the terms "comprising" and "including" are inclusive of other components, elements, integers, steps and the like. Conversely, the term "consisting" and its variants are exclusive of other components, elements, integers, steps and the like. The term "about" encompasses a variation within and including ±10%, unless otherwise specified.

In one embodiment, the expression cassette is designed for human liver-directed expression. Thus, a liver-specific promoter is particularly well suited for the expression cassette. In one embodiment, thyroxin binding globulin promoter is selected. In one embodiment, the TBG promoter has the sequence of nucleotides 442 to 901 of FIG. 1. Alternatively, another liver-specific promoter may be selected. Examples of promoters that are tissue-specific are well known for liver and other tissues (albumin, Miyatake et al., (1997) *J. Virol.*, 71:5124-32; hepatitis B virus core promoter, Sandig et al., (1996) *Gene Ther.*, 3:1002-9; alpha-fetoprotein (AFP), Arbuthnot et al., (1996) *Hum. Gene Ther.*, 7:1503-14), bone osteocalcin (Stein et al., (1997) *Mol. Biol. Rep.*, 24:185-96); bone sialoprotein (Chen et al., (1996) *J Bone Miner. Res.*, 11:654-64), lymphocytes (CD2, Hansal et al., (1998)*J. Immunol.*, 161:1063-8; immunoglobulin heavy chain; T cell receptor chain), neuronal such as neuron-specific enolase (NSE) promoter (Andersen et al., (1993) *Cell. Mol. Neurobiol.*, 13:503-15), neurofilament light-chain gene (Piccioli et al., (1991) *Proc. Natl. Acad. Sci. USA*, 88:5611-5), and the neuron-specific vgf gene (Piccioli et al., (1995) *Neuron*, 15:373-84), among others. Other promoters (not liver-specific) may be selected, but expression cassettes containing same may not have all of the advantages of those with TBG or another liver-specific promoter. Alternatively, a regulatable promoter may be selected. See, e.g., WO 2011/126808B2, incorporated by reference herein.

In one embodiment, the expression cassette comprises one or more expression enhancers. In one embodiment, the expression cassette contains two or more expression enhancers. These enhancers may be the same or may from one another different. For example, an enhancer may include an Alpha mic/bik enhancer. This enhancer may be present in two copies which are located adjacent to one another. Alternatively, the dual copies of the enhancer may be separated by one or more sequences. In still another embodiment, the expression cassette further contains an intron, e.g, the Promega intron. Other suitable introns include those known in the art, e.g., such as are described in WO 2011/126808.

Further, an expression cassette of the invention is provided with a suitable polyadenylation signal. In one embodiment, the polyA sequence is a rabbit globulin poly A. In one embodiment, the polyA sequence is characterized by that of nt 3261-3387 of FIG. 1. Alternatively, another polyA, e.g., a human growth hormone (hGH) polyadenylation sequence, an SV40 polyA, or a synthetic polyA. Still other conventional regulatory elements may be additional or optionally included in an expression cassette.

In one embodiment, the expression cassette is engineered onto a suitable vector, e.g., a plasmid vector using techniques known to those of skill in the art. Optionally, a composition of the invention may contain a first expression cassette comprising the modified human IDUA gene and a second expression cassette comprising a different gene. In still another embodiment, the functional human IDUA may be expressed from a more than one expression cassette, which may be located on a multiple vectors, e.g., as described in WO 2011/126808.

In one embodiment, the expression cassette is carried by the pENN.TBG.hIDUA.nRBG, which plasmid is used to generate a recombinant adeno-associated virus carrying the expression cassette.

Production of AAV Viral Particles

In one embodiment, the invention provides a recombinant adeno-associated virus (rAAV) particle having an AAV capsid and having packaged therein a 5' inverted terminal repeat (ITR), a human alpha-L-iduronidase (hIDUA) gene under the control of regulatory sequences which control expression thereof, and an AAV 3' ITR, wherein said hIDUA gene has a sequence shown in SEQ ID NO: 1 (FIG. 1) or a sequence at least about 95% identical thereto which encodes a functional human alpha-L-iduronidase. One particularly desirable rAAV is AAV2/8.TBG.hIDUA.co.

Methods of preparing AAV-based vectors are known. See, e.g., US Published Patent Application No. 2007/0036760 (Feb. 15, 2007), which is incorporated by reference herein. The use of AAV capsids of AAV8 are particularly well suited for the compositions and methods described herein. The sequences of AAV8 and methods of generating vectors based on the AAV8 capsid are described in U.S. Pat. No. 7,282,199 B2, U.S. Pat. No. 7,790,449, and U.S. Pat. No. 8,318,480, which are incorporated herein by reference. Also well suited for use in the invention are AAV9 capsids. The sequences of AAV9 and methods of generating vectors based on the AAV9 capsid are described in U.S. Pat. No. 7,906,111, which is incorporated by reference herein. However, other AAV capsids may be selected or generated for use in the invention. The sequences of a number of such AAV are provided in the above-cited U.S. Pat. No. 7,282,199 B2, U.S. Pat. No. 7,790,449, U.S. Pat. No. 8,318,480, and U.S. Pat. No. 7,906,111, and/or are available from GenBank. The sequences of any of the AAV capsids can be readily generated synthetically or using a variety of molecular biology and genetic engineering techniques. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, oligonucleotides encoding peptides (e.g., CDRs) or the peptides themselves can generated synthetically, e.g., by the well-known solid phase peptide synthesis methods (Merrifield, (1962) *J. Am. Chem. Soc.*, 85:2149; Stewart and Young, Solid Phase Peptide Synthesis (Freeman, San Francisco, 1969) pp. 27-62). See, also, D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety. These and other suitable production methods are within the knowledge of those of skill in the art and are not a limitation of the present invention.

The recombinant adeno-associated virus (AAV) described herein may be generated using techniques which are known. Such a method involves culturing a host cell which contains a nucleic acid sequence encoding an AAV capsid; a functional rep gene; a expression cassette composed of, at a minimum, AAV inverted terminal repeats (ITRs) and a transgene; and sufficient helper functions to permit packaging of the expression cassette into the AAV capsid protein.

The components required to be cultured in the host cell to package an AAV expression cassette in an AAV capsid may be provided to the host cell in trans. Alternatively, any one or more of the required components (e.g., expression cassette, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contains the rep and/or cap proteins under the control of inducible promoters. Still other stable host cells may be generated by one of skill in the art.

The expression cassette, rep sequences, cap sequences, and helper functions required for producing the rAAV of the invention may be delivered to the packaging host cell in the form of any genetic element which transfer the sequences carried thereon. The selected genetic element may be delivered by any suitable method, including those described herein. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y. Similarly, methods of generating rAAV virions are well known and the selection of a suitable method is not a limitation on the present invention. See, e.g., K. Fisher et al, (1993) *J. Virol.*, 70:520-532 and U.S. Pat. No. 5,478,745.

Unless otherwise specified, the AAV ITRs, and other selected AAV components described herein, may be readily selected from among any AAV. These ITRs or other AAV components may be readily isolated using techniques available to those of skill in the art from an AAV sequence. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

A. The Expression Cassette

The expression cassette is as defined herein. In addition, the expression cassette and/or a vector as described herein may contain additional transgene or regulatory sequences. The expression cassette that is packaged into a capsid protein and delivered to a selected host cell.

1. The Transgene

The invention may include the use of multiple transgenes. Suitable transgenes may be readily selected by one of skill in the art. The selection of the transgene is not considered to be a limitation of this invention.

2. Regulatory Elements

In addition to the major elements identified above for the expression cassette, the vector also includes conventional control elements which are operably linked to the transgene in a manner which permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, (1985) Cell, 41:521-530], the SV40 promoter, the dihydrofolate reductase promoter, the β-actin promoter, the phosphoglycerol kinase (PGK) promoter, and the EF1 promoter [Invitrogen]. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. Examples of inducible promoters regulated by exogenously supplied compounds, include, the zinc-inducible sheep metallothionine (MT) promoter, the dexamethasone (Dex)-inducible mouse mammary tumor virus (MMTV) promoter, the T7 polymerase promoter system [International Patent Publication No. WO 98/10088]; the ecdysone insect promoter [No et al, (1996) Proc. Natl. Acad. Sci. USA, 93:3346-3351], the tetracycline-repressible system [Gossen et al, (1992) Proc. Natl. Acad. Sci. USA, 89:5547-5551], the tetracycline-inducible system [Gossen et al, (1995) Science, 268:1766-1769, see also Harvey et al, (1998) Curr. Opin. Chem. Biol., 2:512-518], the RU486-inducible system [Wang et al, (1997) Nat. Biotech., 15:239-243 and Wang et al, (1997) Gene Ther., 4:432-441] and the rapamycin-inducible system [Magari et al, (1997) J. Clin. Invest., 100:2865-2872], including, e.g., the Argent™ system which is available from Ariad. Other types of inducible promoters which may be useful in this context are those which are regulated by a specific physiological state, e.g., temperature, acute phase, a particular differentiation state of the cell, or in replicating cells only.

Another embodiment of the transgene includes a gene operably linked to a tissue-specific promoter. For instance, if expression in skeletal muscle is desired, a promoter active in muscle should be used. These include the promoters from genes encoding skeletal β-actin, myosin light chain 2A, dystrophin, desmin, MHC, muscle creatine kinase, as well as synthetic muscle promoters with activities higher than naturally-occurring promoters (see Li et al., (1999) Nat. Biotech., 17:241-245). Examples of promoters that are tissue-specific are known for CNS/neuronal include, e.g., neuron-specific enolase (NSE) promoter (Andersen et al., (1993) Cell. Mol. Neurobiol., 13:503-15), neurofilament light-chain gene (Piccioli et al., (1991) Proc. Natl. Acad. Sci. USA, 88:5611-5), and the neuron-specific vgf gene (Piccioli et al., (1995) Neuron, 15:373-84), among others. In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The combination of the transgene, promoter/enhancer, and 5' and 3' AAV ITRs is referred to as an expression cassette for ease of reference herein. Provided with the teachings of this invention, the design of such an expression cassette can be made by resort to conventional techniques.

3. Delivery of the Expression Cassette to an AAV Packaging Host Cell

The expression cassette can be carried on any suitable vector, e.g., a plasmid, which is delivered to a host cell. The plasmids useful in this invention may be engineered such that they are suitable for replication and, optionally, integration in prokaryotic cells, mammalian cells, or both. These plasmids (or other vectors carrying the expression cassette) contain sequences permitting replication of the expression cassette in eukaryotes and/or prokaryotes and selection markers for these systems. Selectable markers or reporter genes may include sequences encoding kanamycin, geneticin, hygromicin or purimycin resistance, among others. The plasmids may also contain certain selectable reporters or marker genes that can be used to signal the presence of the vector in bacterial cells, such as ampicillin resistance. Other components of the plasmid may include an origin of replication and an amplicon, such as the amplicon system employing the Epstein Barr virus nuclear antigen. This amplicon system, or other similar amplicon components permit high copy episomal replication in the cells. Preferably, the molecule carrying the expression cassette is transfected into the cell, where it may exist transiently. Alternatively, the expression cassette may be stably integrated into the genome of the host cell, either chromosomally or as an episome. In certain embodiments, the expression cassette may be present in multiple copies, optionally in head-to-head, head-to-tail, or tail-to-tail concatamers. Suitable transfection techniques are known and may readily be utilized to deliver the expression cassette to the host cell.

Generally, when delivering the vector comprising the expression cassette by transfection, the vector is delivered in an amount from about 5 μg to about 100 μg DNA, about 10 μg to about 50 μg DNA to about $1 \times 10^4$ cells to about $1 \times 10^{13}$ cells, or about $1 \times 10^5$ cells. However, the relative amounts of vector DNA to host cells may be adjusted, taking into consideration such factors as the selected vector, the delivery method and the host cells selected.

B. Packaging Host Cells

In addition to the expression cassette, the host cell contains the sequences which drive expression of an AAV capsid protein of the invention in the host cell and rep sequences of the same source as the source of the AAV ITRs found in the expression cassette, or a cross-complementing source. The packaging host cell also requires helper functions in order to package the rAAV of the invention. Such helper functions are well known in the art and will not be duplicated herein. Similarly, methods for producing suitable vectors having AAV capsids are known. [See, e.g., US Published Patent Application No. US 2007/0036760].

The construct of a rAAV encoding an expression cassette described herein same can be suspended in a physiologically compatible carrier, may be administered to a subject. In one embodiment, the carrier is sterile saline alone or, optionally, with any of a number of buffering solutions (e.g., phosphate buffered saline). Other exemplary carriers include lactose, sucrose, calcium phosphate, gelatin, dextran, agar, pectin, sesame oil, and water. The selection of the carrier is not a limitation of the present invention.

Optionally, the compositions of the invention may contain, in addition to the rAAV and carrier(s), other conventional pharmaceutical ingredients, such as preservatives, or chemical stabilizers. In one embodiment, delivery is via intravenous delivery. However, still other routes of administration may be selected. Alternatively or additionally, routes of administration may be combined, if desired.

In one embodiment, the invention includes a lyophilized composition which contains an rAAV as described herein, or a mixture of rAAV, in lyophilized form. Optionally, one or more stabilizers or preservatives is present in this composition. Suitably, for use, a lyophilized composition is reconstituted with a suitable diluent, e.g., sterile saline or a buffered saline.

Dosages of the viral vector will depend primarily on factors such as the condition being treated, the age, weight and health of the patient, and may thus vary among patients. For example, a therapeutically effective dosage of the viral vector is generally in the range of from about 0.1 mL to about 100 mL, or about 0.1 mL to about 10 mL, or about 0.1 mL to about 5 mL, or about 0.5 mL to about 1 mL, of solution containing concentrations of from about $3 \times 10^9$ to $3 \times 10^{13}$ genomes viral vector (particles)/mL aqueous suspending agent. Another exemplary dosage is about $3 \times 10^9$ to $3 \times 10^{13}$ AAV genomes per 1 kg. One suitable volume is about 1 mL. In another embodiment, a therapeutically effective dose of the rAAV construct is in the range of about 0.001 ng to about 1000 mg/70 kg animal, which may be delivered in a single dosage or over a series of two or more doses. Other suitable dosages may be determined. The dosage will be adjusted to balance the therapeutic benefit against any side effects and such dosages may vary depending upon the therapeutic application for which the recombinant vector is employed.

Methods of Treatment

The compositions of the present invention avoid complications of enzyme replacement therapy related to immune response to the recombinant enzyme which can range from mild to full-blown anaphylaxis as well as complications of life-long peripheral access such as local and systemic infections. Further, in contrast to ERT, the composition of the invention does not require long term, repeated weekly injections. Without wishing to be bound by theory, the liver-directed therapeutic method described herein is believed to be useful for correcting the central nervous system phenotype associated with MPSI disorders by providing efficient, long-term gene transfer afforded by vectors with high transduction efficiency could provide continuous, elevated circulating IDUA levels, which provides therapeutic leverage across the blood brain barrier. In addition, AAV liver gene transfer may provide active tolerance and prevent antibody formation against the enzyme.

A method for treating type I mucopolysaccharidosis comprising delivering a therapeutically effective amount of a modified hIDUA expression cassette as described herein is provided. Also provided is a method for treating and/or ameliorating the symptoms of Hurler, Hurler-Scheie and Scheie syndromes.

In one embodiment, the rAAV is delivered intravenously.

In another embodiment, the rAAV is delivered in an amount of about $3 \times 10^9$ to about $3 \times 10^{12}$ is delivered to the subject. While a single administration of the rAAV is anticipated to be effective, since the liver is a regenerative organ, administration by be repeated (e.g., quarterly, bi-annually, annually, or as otherwise needed. Optionally, an initial dose of a therapeutically effective amount may be delivered over split infusion sessions, taking into consideration the age and ability of the subject to tolerate infusions. However, repeated weekly injections of a full therapeutic dose are not required, providing an advantage to the patient in terms of both comfort and therapeutic outcome.

The following examples are illustrative only and are not a limitation on the invention described herein.

Example 1—Transgene and Vector Production

A modified nucleotide sequence encoding a functional human alpha-L-iduronidase was synthesized. The resulting sequence is particularly well suited for human expression and has less than about 90% identical to the functional human IDUA gene (hIDUA; Genbank NP000194.2). The resultant transgene was then inserted into a plasmid containing cis elements necessary for packaging into an AAV vector available from UPenn Vector Core using engineered MluI and SalI sites. Gene expression was driven by the human thyroid binding globulin (TBG, Hayashi Y, Mori Y, Janssen O E, et al. Human thyroxine-binding globulin gene: complete sequence and transcriptional regulation. Mol Endocrinol 1993; 7: 1049-1060]. The resulting plasmid, shown in FIG. 2, pENN.AAV.TBG.PI.hIDUA.RGB contains the modified hIDUA gene under the control of expression control sequences including the liver-specific TBG promoter. The plasmid further contains the AAV2 5' ITR, tandem repeats of the alpha mic/bic enhancers, the TBG promoter, a Promega intron sequence, the modified human IDUA gene of SEQ ID NO: 1, a rabbit globulin poly A, and an AAV2-3' ITR.

Large scale vector preparations were made essentially as described by Lock et al. [Rapid, simple, and versatile manufacturing of recombinant adeno-associated viral vectors at scale. Hum Gene Ther 21(10): 1259-1271. (2010)]. PEI-based transfections were performed in 10 layer cell stacks containing 75% confluent monolayers of HEK293 cells. 10 L of feedstock culture medium from the cell stacks was clarified and then concentrated by tangential flow filtration. The concentrated clarified feedstock was purified over iodixanol (Optiprep; Sigma Chemical Co., St Louis, Mo.) gradients. All fractions directly below a visible contaminating protein band were collected and pooled. Pooled fractions were diafiltered against of PBS/35 mM NaCl and concentrated using Amicon Ultra 15 spin concentrators (Millipore). Glycerol was added to the diafiltered, concentrated product to 5% final and the preparation was aliquoted and stored at −80° C. The resulting vectors are termed herein AAV8.TBG.hIDUA or AAV2/8.TBG.hIDUA. In certain locations, the recombinant AAV particles are referred to as AAV8.TBG.hIDUAco or AAV2/8.TBG.hIDUAco. The plasmid further contains the AAV2 5' ITR, tandem repeats of the alpha mic/bic enhancers, the TBG promoter, a Promega intron sequence, the modified human IDUA gene of SEQ ID NO: 1, a rabbit globulin poly A, and an AAV2-3' ITR.

Example 2

A. Cell Based Assays

HEK 293 cells were maintained in growth medium containing Dulbecco's Modified Eagle Medium (DMEM; Gibco®, Life Technologies™) with 5% fetal bovine serum (FBS; XXX), 1% penicillin/streptomycin (p/s; Life Technologies™). Plasmid DNA transfections were carried out using Lipofectamine™2000 (Invitrogen™, Life Technologies™) according to the manufacturer's recommendations. Briefly, cells were plated at a density of 5×10^5 cells/well in 6-well tissue culture dishes in transfection medium (DMEM+5% FBS, no p/s) and allowed to adhere overnight at 37° in 5% $CO_2$. On the next day, cells were checked for 90-95% confluency and the media was refreshed. Plasmid DNA and Lipofectamine™2000 were diluted with Opti-MEM I® Reduced Serum Medium (without serum) for a final ratio of 1:2.5 (DNA: Lipofectamine™2000). The Lipofectamine™2000 transfection solution was incubated for five minutes at 22° C. before mixing with the DNA solution. This final transfection mixture containing the DNA: Lipofectamine™2000 solution was incubated further for 20 minutes (22° C.) before addition to the wells containing cells and media. Mock cells received no plasmid DNA and a plasmid encoding for eGFP was used as a transfection control. Three wells were transfected for each construct tested. Cells were incubated at 37° in 5% $CO_2$; media was replaced with growth media four hours later. Contents of each well were harvested 72 hours later and collected at 4000 rpm for 15 minutes at 4° C. Cells were resuspended in 100 μls/well lysis buffer (0.2% Triton X-100, 0.9% NaCl, pH4.0) and freeze/thawed three times with vortexing. In addition, lysates were treated with Benzonase for 30 minutes at 37° C. before the final freeze/thaw. Cell debris was pelleted at 10 000 rpm (4° C.) for 10 minutes and final clarified cell lysates were placed on ice and immediately assayed for enzyme activity.

B. Tissue Lysis and Protein Extraction

Frozen tissues were semi-thawed in a box on a bed of dry ice and small pieces of wet tissue were cut (~20 mgs, ~10 mgs of spleen) up in a small petri dish. The pre-processed tissues were then submerged in a 2-ml eppendorph with 1 ml lysis buffer (0.2% Triton X-100, 0.9% NaCl, pH4.0) and a 5 mm steel bead. Samples were homogenized on a tissue-lyzer at 30 Hz for 2 minutes. Homogenized samples were briefly spun at 6000 rpm for 30 seconds and the 5 mm steel beads were removed. Tissue lysates were further disrupted by sonication using a 1-1/16" diameter microhorn and frozen overnight at −80° C. Processed samples were thawed the next day at 22° C. and clarified by centrifugation (10 000 rpm/10 minutes/4° C.). Floating lipid layers from brain, or other fatty tissues, were aspirated before assay. Samples were then stored on wet ice and assayed immediately for enzyme activity.

C. Protein Estimation

Total protein was estimated using the Coomassie based Bradford assay (Thermo Scientific) following the manufacturer's protocol. Briefly, a standard curve was set up using bovine serum albumin (BSA) to generate a working range from 1-25m/ml and a blank accounting for the protein dilution buffer with no BSA. Samples were diluted twofold from 1/300-1/1200 and mixed at a 1:1 ratio of diluted protein: Bradford reagent in a 96-well flat-bottom dish. Samples were allowed to equilibrate at 22° C. for 15 minutes and absorbance values were collected on a plate reader at the suggested wavelength of 595 nm. Raw values were converted to μg/ml concentrations using the standard curve with blank correction. Microgram quantities were then converted and reported in milligrams.

D. Enzyme Activity Assays

IDUA enzyme activity was assayed using 4-Methylumbelliferyl alpha-L-Idopyranosiduronic Acid, Cyclohexylammonium Salt (4-MU-Ido; Toronto Research Chemicals, Inc.) as a substrate according to previously published methods [Kakkis et al, Mol Genet Metab, 2001 March; 72(3): 199-208]. Briefly, 5-15 μls of lysates, or serum, were brought up to 100 μls with double distilled water ($ddH_2O$) and 100 μls of 100 μM 4-MU-Ido substrate, diluted with reaction buffer (0.1M sodium acetate pH3.5, 0.15M NaCl, 0.05% Triton X-100) was combined in a methylacrylate cuvette (Thermo Scientific). Reactions were incubated for 1-3 hours in a 37° C. water bath and ended with the addition of a 1× stop buffer (290 mM glycine, 180 mM sodium carbonate, pH 10.5). Products were read on a QuantiFluor™-ST (Promega) through the UV channel (Ex 365 nm, Em 440-470 nm). Raw fluorescence values were recorded and converted to nmol/ml/hr using a standard curve of known quantities of 4-Methylumbelliferone (M-5410; Biosynth®). Cell and tissue lysates were normalized to estimated protein values (nmol/mg/hr; see methods section entitled "protein estimation").

E. DNA Extraction and Genome Copy Analysis

Taqman PCR was used to determine the vector DNA load in diploid cells. For detection and quantification of vector genomes by real-time PCR, total cellular DNA was extracted from tissues using a QIAamp DNA Mini Kit (Qiagen, Valencia, Calif., USA). Primer and probe sets were designed to target the nRBG polyA region of the vector, using the following sequences; forward: GCCAAAAAT-TATGGGGACAT, reverse: ATTCCAACACACTATTG-CAATG, probe: 6FAM-ATGAAGCCCCTTGAGCATCT-GACTTCT-TAMRA. Standard curves for vector genome quantification were established with the cis plasmids used for the production of the corresponding vector. The PCR was performed with a TaqMan Universal PCR Master Mix (Applied Biosystems, Foster City, Calif., USA) with 200 ng total cellular DNA as template, 300 nM primers, and 200 nM probes each. Cycles were for 2 min at 50° C., 10 min at 95° C., 40 cycles of 15 s at 95° C., and 1 min at 60° C.

F. Immunoblotting

Immunoblotting was performed according to standard methods. In brief, the NuPAGE gel system (Life Technologies), 4-12% bis-tris gels was used. Transfer was following 30 minutes at 20V to a PVDF membrane. The block was 10% NFDM in T-PBS (overnight). The primary MAb was mouse anti-human IDUA 1:300 (1.5 hours); 1% NFDM in T-PBS. Secondary: HRP-linked rabbit anti-mouse 1:3000 (1 hr); 1% NFDM in T-PBS Detection was by SuperSignal West Dura Chemiluminescent Substrate (Thermo Scientific), 30 second exposure on x-ray film.

Example 3—In Vivo Studies in Mice and Dogs

IDUA deficiencies can be found in dogs, allowing for study of the disease and therapies in a large animal. MPS I dogs carry a recessive (null) mutation in the IDUA gene, in which a G>A mutation in the donor splice site of intron 1 creates a premature termination codon at the exon-intron junction [Menon, K. P., P. T. Tieu, and E. F. Neufeld, Architecture of the canine IDUA gene and mutation underlying canine mucopolysaccharidosis I. Genomics, 1992. 14(3): p. 763-8.]. The course of disease in the dog is analogous to Hurler-Scheie syndrome; disease manifestations include significant skeletal disease, including chest deformity.

Urine GAG analysis is a biochemical marker used to determine efficacy of treatments for MPS I in the clinical setting.

Accumulation of glycosaminoglycans (GAGs) were evaluated in major organs by Alcian Blue (pH1) stain of paraffin sections. The accumulation of unprocessed GAG within cells are particularly well visualized on 1 µm thin sections from plastic-embedded tissues stained with Toluidine Blue. Thin sections (1 µm) of epon-embedded tissues, stained with Toluidine Blue. This shows cells containing storage material ("foamy, sponge cells").

Immunohistochemistry was performed with antibody against ganglioside GM3 in brain. Shows abnormal storage of GM3 in neurons. The cortex was evaluated in dogs and cortex and hypothalamus in mice. Expression of human IDUA in liver was evaluated by immunofluorescence.

A. Mouse Studies

AAV8.TBG.modified hIDUA was prepared as described in Example 1. Mice (about 3 months) were injected intravenously at doses of about $1 \times 10^{11}$ GC, $3 \times 10^{10}$ GC, $3 \times 10^9$ GC, $1 \times 10^9$ GC and evaluated ~2 weeks post injection.

The results showed diminished or complete absence of GAG staining in the animals dosed at $1 \times 10^{11}$, $3 \times 10^{10}$, and $3 \times 10^9$. In these animals, diminished or complete absence of storage lesions was observed in thin sections.

In the animals dosed at $1 \times 10^9$ GAG storage looks more or less as in untreated mice and storage lesions look more or less as in untreated mice For GM3 storage, only the animals dosed at $1 \times 10^{11}$ GC and $3 \times 10^{10}$ GC have been evaluated, and a very weak improvement in GM3 storage in neurons was observed.

Strong expression (100% of hepatocytes) of IDUA was observed in animals dosed at $1 \times 10^{11}$ GC. This drops off with lower doses, with only very few positive hepatocytes visible at $1 \times 10^9$ GC.

B. Canine Studies

AAV8.TBG.modified hIDUA was prepared as described in Example 1. Dogs (about 8 months age) were injected intravenously at a dose of $1 \times 10^{11}$ GC and evaluated after four months post injection (i.e. 1 year old).

This study shows reversal of storage lesions. More particularly, virtually complete clearance of GAG storage in all major organs is seen by Alcian Blue stain. No storage lesions are observed in heart, kidney or liver thin sections. A reduction or complete clearance of GM3 accumulation is observed in neurons. Expression of IDUA in liver is observed by immunofluorescence in >95% of hepatocytes.

Example 4—Treatment of Hurler-Scheie with AAV2/8.TBG.hIDUA

AAV8-mediated gene transfer of IDUA will be evaluated in Hurler-Scheie patients. The subjects would receive a single infusion of vector into a peripheral vein which based on pre-clinical data should lead to stable production of the enzyme at levels that are close to what is obtained in normal subjects. The trial may involve different doses of vector for example, $3 \times 10^{11}$ GC/kg; $1 \times 10^{12}$ GC/kg; $3 \times 10^{12}$ GC/kg and please add dose range. The most non-invasive assessment of efficacy is the level of urine GAG which are elevated in the disease and partially corrected following ERT. Transgene engraftment and its level of expression will be determined by measuring serum IDUA. Urine GAG will also be measured before and after gene therapy.

Sequence Listing Free Text

The following information is provided for sequences containing free text under numeric identifier <223>.

| SEQ ID NO: (containing free text) | Free text under <223> |
|---|---|
| SEQ ID NO: 3 | <220> |
| | <221> repeat_region |
| | <222> (1) . . . (130) |
| | <223> 5' ITR |
| | <220> |
| | <221> enhancer |
| | <222> (221) . . . (320) |
| | <223> Alpha mic/bik |
| | <220> |
| | <221> enhancer |
| | <222> (327) . . . (426) |
| | <223> Alpha mic/bik |
| | <220> |
| | <221> promoter |
| | <222> (442) . . . (901) |
| | <223> TBG promoter |
| | <220> |
| | <221> TATA_signal |
| | <222> (885) . . . (888) |
| | <220> |
| | <221> Intron |
| | <222> (1027) . . . (1159) |
| | <223> intron 1 |
| | <220> |
| | <221> CDS |
| | <222> (1251) . . . (3212) |
| | <223> human alpha-L-IDUE |
| | <220> |
| | <221> polyA_signal |
| | <222> (3261) . . . (3387) |
| | <220> |
| | <221> repeat_region |
| | <222> (3476) . . . (3605) |
| | <223> 3' ITR (located on complement) |
| | <220> |
| | <221> rep_origin |
| | <222> (3782) . . . (4220) |
| | <223> f1\ori (located on complement) |
| | <220> |
| | <221> rep_origin |
| | <222> (4249) . . . (4891) |
| | <223> pUC\origin of replication\ |
| | <220> |
| | <221> misc_feature |
| | <222> (5566) . . . (6381) |
| | <223> kanamycin resistance located on complementary strand |

A sequence listing labelled "Z6622PCT_ST25.txt" is being filed herewith in electronic form; this sequence listing is hereby incorporated by reference. All publications, patents, and patent applications cited in this application, including priority application U.S. Patent Application No. 61/788,724, filed Mar. 15, 2013, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A recombinant adeno-associated virus (rAAV) particle having an AAV capsid and having packaged therein a 5' inverted terminal repeat (ITR), a human alpha-L-iduronidase (hIDUA) gene under the control of regulatory sequences which control expression thereof, and an AAV 3' ITR, wherein said hIDUA gene has a sequence of SEQ ID NO: 1 or a sequence at least about 95% identical to SEQ ID NO: 1 which encodes a functional human alpha-L-iduronidase.

2. The rAAV particle according to claim 1, wherein said hIDUA gene is expressed under the control of a liver-specific promoter.

3. The rAAV particle according to claim 2, wherein the promoter is a thyroxin binding globulin (TBG) promoter.

4. The rAAV particle according to claim 1, wherein the regulatory sequences comprise one or more enhancers.

5. The rAAV particle according to claim 4, wherein the enhancers are the same or different.

6. The rAAV particle according to claim 4, wherein the enhancers are selected from the group consisting of an intron, a cytomegalovirus (CMV) enhancer, and an Alpha mic/bik enhancer.

7. The rAAV particle according to claim 6, wherein more than one copy of a selected enhancer are present in the vector.

8. The rAAV particle according to claim 7, wherein the more than one copy of the enhancer are located in tandem.

9. The rAAV particle according to claim 1, wherein the rAAV particle comprises an AAV capsid selected from AAV8 and AAV9.

10. The rAAV particle according to claim 9, wherein the rAAV particle is pseudotyped.

11. The rAAV particle according to claim 1, wherein the ITRs are from an AAV2.

12. The rAAV particle according to claim 1, having an AAV8 capsid and having packaged therein an AAV2 5' ITR, a hIDUA gene of SEQ ID NO: 1, under the control of regulatory sequences which control expression thereof, and an AAV2 3' ITR, wherein the control regulatory sequences comprises a liver-specific TBG promoter, tandem repeats of alpha mic/bic enhancers, an intron sequence, and a poly A.

13. A composition useful for treating mucopolysaccharidosis type I (MPS I) comprising the rAAV particle according to claim 1 and a pharmaceutically acceptable carrier.

14. A method for treating MPS I comprising delivering an effective amount of a composition comprising a pharmaceutically acceptable carrier and the rAAV particle according to claim 1 to a subject.

15. The method according to claim 14, wherein said rAAV particle is delivered intravenously.

16. The method according to claim 15, wherein about $3 \times 10^9$ to about $3 \times 10^{12}$ genome copies of the rAAV is delivered to the subject.

17. The rAAV particle according to claim 1, wherein the functional human alpha-L-iduronidase is selected from:
(a) about amino acid (aa) 1 to about aa 653 of SEQ ID NO: 2;
(b) a synthetic human enzyme comprising a heterologous leader sequence fused to about aa 27 to about aa 653 of SEQ ID NO: 2; and
(c) a variant of amino acid sequence of SEQ ID NO:2 having one or more of the modifications comprising: an H to Q reduction at amino acid position 82 (SEQ ID NO:8); a change from R to Q at position 105 (SEQ ID NO: 9); a change from G to R at position 116 (SEQ ID NO: 10); a change from V to A at position 279 (SEQ ID NO: 11); a change from L to R at position 346 (SEQ ID NO: 12); a change from A to T at position 361 (SEQ ID NO: 13); a change from H to N at position 449 (SEQ ID NO: 14); a change from V to I at position 454 (SEQ ID NO: 15); a change from A to T at position 591 (SEQ ID NO: 16); and a change from A to T at position 622 (SEQ ID NO: 17).

18. The rAAV particle according to claim 1, wherein regulatory sequences further comprise a poly A.

19. The rAAV particle according to claim 1, wherein the hIDUA has the sequence at least 95% identical to SEQ ID NO: 1 which encodes a functional human alpha-L-iduronidase.

20. The rAAV particle according to claim 1, wherein the hIDUA has the sequence at least 97% identical to SEQ ID NO: 1 which encodes a functional human alpha-L-iduronidase.

21. The rAAV particle according to claim 1, wherein the hIDUA has the sequence at least 99% identical to SEQ ID NO: 1 which encodes a functional human alpha-L-iduronidase.

22. The rAAV particle according to claim 1, wherein the hIDUA gene has the sequence of SEQ ID NO: 1.

* * * * *

SEQUENCE LISTING

<160> NUMBER OF SEQ ID NOS: 17

<210> SEQ ID NO 1
<211> LENGTH: 1971
<212> TYPE: DNA
<213> ORGANISM: Homo sapiens
<220> FEATURE:
<221> NAME/KEY: CDS
<222> LOCATION: (1)..(1971)

<400> SEQUENCE: 1

| | | | | | | | | | | | | | | | | |
|---|---|---|---|---|---|---|---|---|---|---|---|---|---|---|---|---|
| atg | cgg | ccc | ctg | agg | cct | aga | gct | gct | ctg | ctg | gca | ctg | ctg | gcc | agt | 48 |
| Met | Arg | Pro | Leu | Arg | Pro | Arg | Ala | Ala | Leu | Leu | Ala | Leu | Leu | Ala | Ser | |
| 1 | | | | 5 | | | | | 10 | | | | | 15 | | | ctg ctg gct gcc cct cct gtg gcc cct gcc gaa gcc cct cac ctg gtg   96
Leu Leu Ala Ala Pro Pro Val Ala Pro Ala Glu Ala Pro His Leu Val
            20                  25                  30 cat gtg gat gcc gcc aga gcc ctg tgg cct ctg cgg aga ttc tgg cgg   144
His Val Asp Ala Ala Arg Ala Leu Trp Pro Leu Arg Arg Phe Trp Arg
        35                  40                  45 agc acc ggc ttt tgc ccc cca ctg cct cac agc cag gcc gac cag tac   192
Ser Thr Gly Phe Cys Pro Pro Leu Pro His Ser Gln Ala Asp Gln Tyr
    50                  55                  60 gtg ctg agc tgg gac cag cag ctg aac ctg gcc tac gtg ggc gcc gtg   240
Val Leu Ser Trp Asp Gln Gln Leu Asn Leu Ala Tyr Val Gly Ala Val
65                  70                  75                  80 ccc cac aga ggc atc aaa cag gtg aga acc cac tgg ctg ctg gaa ctg   288
Pro His Arg Gly Ile Lys Gln Val Arg Thr His Trp Leu Leu Glu Leu
                85                  90                  95 gtg aca acc cgg ggc tcc acc ggc aga ggc ctg agc tac aac ttc acc   336
Val Thr Thr Arg Gly Ser Thr Gly Arg Gly Leu Ser Tyr Asn Phe Thr
            100                 105                 110 cac ctg gac ggc tac ctg gac ctg ctg aga gag aac cag ctg ctg ccc   384
His Leu Asp Gly Tyr Leu Asp Leu Leu Arg Glu Asn Gln Leu Leu Pro
        115                 120                 125 ggc ttc gag ctg atg ggc agc gcc agc ggc cac ttc acc gac ttc gag   432
Gly Phe Glu Leu Met Gly Ser Ala Ser Gly His Phe Thr Asp Phe Glu
    130                 135                 140 gac aag cag caa gtc ttt gag tgg aag gac ctg gtg tcc agc ctg gcc   480
Asp Lys Gln Gln Val Phe Glu Trp Lys Asp Leu Val Ser Ser Leu Ala
145                 150                 155                 160 aga cgg tac atc ggc aga tac gga ctg gcc cac gtg tcc aag tgg aac   528
Arg Arg Tyr Ile Gly Arg Tyr Gly Leu Ala His Val Ser Lys Trp Asn
                165                 170                 175 ttc gag aca tgg aac gag ccc gac cac cac gac ttc gac aac gtg tca   576
Phe Glu Thr Trp Asn Glu Pro Asp His His Asp Phe Asp Asn Val Ser
            180                 185                 190 atg acc atg cag ggc ttt ctg aac tac tac gac gcc tgc tcc gag ggc   624
Met Thr Met Gln Gly Phe Leu Asn Tyr Tyr Asp Ala Cys Ser Glu Gly
        195                 200                 205 ctg aga gcc gcc agt cct gcc ctg aga ctg ggc gga ccc ggc gat agc   672
Leu Arg Ala Ala Ser Pro Ala Leu Arg Leu Gly Gly Pro Gly Asp Ser
    210                 215                 220 ttc cac acc ccc cca aga agc ccc ctg agc tgg ggc ctg ctg aga cac   720
Phe His Thr Pro Pro Arg Ser Pro Leu Ser Trp Gly Leu Leu Arg His
225                 230                 235                 240 tgc cac gac ggc acc aat ttc ttc acc ggc gag gcc ggc gtg cgg ctg   768
Cys His Asp Gly Thr Asn Phe Phe Thr Gly Glu Ala Gly Val Arg Leu
                245                 250                 255 gac tac atc agc ctg cac cgg aag ggc gcc aga agc agc atc agc atc   816
Asp Tyr Ile Ser Leu His Arg Lys Gly Ala Arg Ser Ser Ile Ser Ile -continued

```
          260              265              270
ctg gaa cag gaa aag gtc gtc gcc cag cag atc cgg cag ctg ttc ccc        864
Leu Glu Gln Glu Lys Val Val Ala Gln Gln Ile Arg Gln Leu Phe Pro
        275              280              285 aag ttc gcc gac acc ccc atc tac aac gac gag gcc gac ccc ctg gtg        912
Lys Phe Ala Asp Thr Pro Ile Tyr Asn Asp Glu Ala Asp Pro Leu Val
        290              295              300 gga tgg tca ctg cct cag cct tgg aga gcc gac gtg acc tac gcc gct        960
Gly Trp Ser Leu Pro Gln Pro Trp Arg Ala Asp Val Thr Tyr Ala Ala
305              310              315              320 atg gtg gtg aaa gtg atc gcc cag cat cag aac ctg ctg gcc aac           1008
Met Val Val Lys Val Ile Ala Gln His Gln Asn Leu Leu Leu Ala Asn
                325              330              335 acc acc agc gcc ttc cct tac gcc ctg ctg agc aac gac aac gcc ttc       1056
Thr Thr Ser Ala Phe Pro Tyr Ala Leu Leu Ser Asn Asp Asn Ala Phe
            340              345              350 ctg agc tac cac ccc cac ccc ttc gcc cag aga acc ctg acc gcc cgg       1104
Leu Ser Tyr His Pro His Pro Phe Ala Gln Arg Thr Leu Thr Ala Arg
        355              360              365 ttc cag gtg aac aac acc aga ccc ccc cac gtg cag ctg ctg aga aag       1152
Phe Gln Val Asn Asn Thr Arg Pro Pro His Val Gln Leu Leu Arg Lys
370              375              380 ccc gtg ctg acc gct atg gga ctg ctg gct ctg ctg gac gag gaa cag       1200
Pro Val Leu Thr Ala Met Gly Leu Leu Ala Leu Leu Asp Glu Glu Gln
385              390              395              400 ctg tgg gcc gaa gtg tcc cag gcc ggc acc gtg ctg gac agc aat cat       1248
Leu Trp Ala Glu Val Ser Gln Ala Gly Thr Val Leu Asp Ser Asn His
                405              410              415 aca gtg ggc gtg ctg gcc tcc gcc cac aga cct cag gga ccc gcc gat       1296
Thr Val Gly Val Leu Ala Ser Ala His Arg Pro Gln Gly Pro Ala Asp
            420              425              430 gct tgg cgg gct gcc gtg ctg atc tac gcc agc gac gat acc aga gcc       1344
Ala Trp Arg Ala Ala Val Leu Ile Tyr Ala Ser Asp Asp Thr Arg Ala
        435              440              445 cac ccc aac aga tcc gtg gcc gtg acc ctg cgg ctg aga ggc gtg cca       1392
His Pro Asn Arg Ser Val Ala Val Thr Leu Arg Leu Arg Gly Val Pro
450              455              460 cca ggc cct gga ctg gtg tac gtg acc aga tac ctg gac aac ggc ctg       1440
Pro Gly Pro Gly Leu Val Tyr Val Thr Arg Tyr Leu Asp Asn Gly Leu
465              470              475              480 tgc agc ccc gac ggc gaa tgg cgc aga ctg ggc aga cct gtg ttc ccc       1488
Cys Ser Pro Asp Gly Glu Trp Arg Arg Leu Gly Arg Pro Val Phe Pro
                485              490              495 acc gcc gag cag ttc cgg cgg atg aga gcc gct gag gat cct gtg gct       1536
Thr Ala Glu Gln Phe Arg Arg Met Arg Ala Ala Glu Asp Pro Val Ala
            500              505              510 gct gcc cct aga cct ctg cct gct ggc ggc aga ctg acc ctg agg ccc       1584
Ala Ala Pro Arg Pro Leu Pro Ala Gly Gly Arg Leu Thr Leu Arg Pro
        515              520              525 gct ctg aga ctg cct agt ctg ctg ctg gtg cac gtg tgc gcc agg ccc       1632
Ala Leu Arg Leu Pro Ser Leu Leu Leu Val His Val Cys Ala Arg Pro
530              535              540 gag aag cct ccc ggc cag gtg aca aga ctg aga gcc ctg ccc ctg acc       1680
Glu Lys Pro Pro Gly Gln Val Thr Arg Leu Arg Ala Leu Pro Leu Thr
545              550              555              560 cag ggc cag ctg gtg ctg gtg tgg tcc gat gag cac gtg ggc agc aag       1728
Gln Gly Gln Leu Val Leu Val Trp Ser Asp Glu His Val Gly Ser Lys
                565              570              575 tgc ctg tgg acc tac gag atc cag ttc agc cag gac ggc aag gcc tac       1776
```

```
                Cys Leu Trp Thr Tyr Glu Ile Gln Phe Ser Gln Asp Gly Lys Ala Tyr
                                580                 585                 590 acc ccc gtg tcc cgg aag ccc agc acc ttc aac ctg ttc gtg ttc agc                    1824
Thr Pro Val Ser Arg Lys Pro Ser Thr Phe Asn Leu Phe Val Phe Ser
            595                 600                 605 ccc gat aca ggc gcc gtg tcc ggc tct tat aga gtg cgg gcc ctg gac                    1872
Pro Asp Thr Gly Ala Val Ser Gly Ser Tyr Arg Val Arg Ala Leu Asp
    610                 615                 620 tac tgg gcc aga ccc ggc cct ttc agc gac ccc gtg ccc tac ctg gaa                    1920
Tyr Trp Ala Arg Pro Gly Pro Phe Ser Asp Pro Val Pro Tyr Leu Glu
625                 630                 635                 640 gtg ccc gtg cct aga ggc ccc cct agc ccc ggc aac cct tga gtc gac                    1968
Val Pro Val Pro Arg Gly Pro Pro Ser Pro Gly Asn Pro     Val Asp
                645                 650                     655 ccg                                                                                 1971
Pro
```

<210> SEQ ID NO 2
<211> LENGTH: 653
<212> TYPE: PRT
<213> ORGANISM: Homo sapiens

<400> SEQUENCE: 2

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
```

```
                260                 265                 270
Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 3
<211> LENGTH: 6863
<212> TYPE: DNA
<213> ORGANISM: Artificial sequence
```

```
<220> FEATURE:
<223> OTHER INFORMATION: Synthetic (plasmid carrying hIDUA)
<220> FEATURE:
<221> NAME/KEY: repeat_region
<222> LOCATION: (1)..(130)
<223> OTHER INFORMATION: 5' ITR
<220> FEATURE:
<221> NAME/KEY: enhancer
<222> LOCATION: (221)..(320)
<223> OTHER INFORMATION: Alpha mic/bik
<220> FEATURE:
<221> NAME/KEY: enhancer
<222> LOCATION: (327)..(426)
<223> OTHER INFORMATION: Alpha mic/bik
<220> FEATURE:
<221> NAME/KEY: promoter
<222> LOCATION: (442)..(901)
<223> OTHER INFORMATION: TBG promoter
<220> FEATURE:
<221> NAME/KEY: TATA_signal
<222> LOCATION: (885)..(888)
<220> FEATURE:
<221> NAME/KEY: Intron
<222> LOCATION: (1027)..(1159)
<223> OTHER INFORMATION: intron 1
<220> FEATURE:
<221> NAME/KEY: CDS
<222> LOCATION: (1251)..(3212)
<223> OTHER INFORMATION: human alpha-L-IDUE
<220> FEATURE:
<221> NAME/KEY: polyA_signal
<222> LOCATION: (3261)..(3387)
<220> FEATURE:
<221> NAME/KEY: repeat_region
<222> LOCATION: (3476)..(3605)
<223> OTHER INFORMATION: 3' ITR (located on complement)
<220> FEATURE:
<221> NAME/KEY: rep_origin
<222> LOCATION: (3782)..(4220)
<223> OTHER INFORMATION: f1øri (located on complement)
<220> FEATURE:
<221> NAME/KEY: rep_origin
<222> LOCATION: (4249)..(4891)
<223> OTHER INFORMATION: pUCørigin of replication
<220> FEATURE:
<221> NAME/KEY: misc_feature
<222> LOCATION: (5566)..(6381)
<223> OTHER INFORMATION: kanamycin resistance located on complementary
      strand

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gaattcgccc ttaagctagc aggttaattt ttaaaaagca     240
gtcaaaagtc caagtggccc ttggcagcat ttactctctc tgtttgctct ggttaataat     300
ctcaggagca caaacattcc agatccaggt taattttttaa aaagcagtca aaagtccaag     360
tggcccttgg cagcatttac tctctctgtt tgctctggtt aataatctca ggagcacaaa     420
cattccagat ccggcgcgcc agggctggaa gctacctttg acatcatttc ctctgcgaat     480
gcatgtataa tttctacaga acctattaga aaggatcacc cagcctctgc ttttgtacaa     540 ctttcccctta aaaaactgcc aattccactg ctgtttggcc caatagtgag aacttttttcc     600 tgctgcctct tggtgctttt gcctatggcc cctattctgc ctgctgaaga cactcttgcc     660
agcatggact taaaccccctc cagctctgac aatcctcttt ctcttttgtt ttacatgaag     720
ggtctggcag ccaaagcaat cactcaaagt tcaaacctta tcattttttg ctttgttcct     780
cttggccttg gttttgtaca tcagctttga aaataccatc ccagggttaa tgctggggtt     840
```

```
aatttataac taagagtgct ctagttttgc aatacaggac atgctataaa aatggaaaga    900
tgttgctttc tgagagacag ctttattgcg gtagtttatc acagttaaat tgctaacgca    960
gtcagtgctt ctgacacaac agtctcgaac ttaagctgca gaagttggtc gtgaggcact   1020
gggcaggtaa gtatcaaggt tacaagacag gtttaaggag accaatagaa actgggcttg   1080
tcgagacaga gaagactctt gcgtttctga taggcaccta ttggtcttac tgacatccac   1140
tttgcctttc tctccacagg tgtccactcc cagttcaatt acagctctta aggctagagt   1200
acttaatacg actcactata ggctagcctc gagaattcac gcgtgccacc atg cgg      1256
                                                       Met Arg
                                                        1 ccc ctg agg cct aga gct gct ctg ctg gca ctg ctg gcc agt ctg ctg     1304
Pro Leu Arg Pro Arg Ala Ala Leu Leu Ala Leu Leu Ala Ser Leu Leu
         5                  10                  15 gct gcc cct cct gtg gcc cct gcc gaa gcc cct cac ctg gtg cat gtg     1352
Ala Ala Pro Pro Val Ala Pro Ala Glu Ala Pro His Leu Val His Val
         20                  25                  30 gat gcc gcc aga gcc ctg tgg cct ctg cgg aga ttc tgg cgg agc acc     1400
Asp Ala Ala Arg Ala Leu Trp Pro Leu Arg Arg Phe Trp Arg Ser Thr
35                  40                  45                  50 ggc ttt tgc ccc cca ctg cct cac agc cag gcc gac cag tac gtg ctg     1448
Gly Phe Cys Pro Pro Leu Pro His Ser Gln Ala Asp Gln Tyr Val Leu
                 55                  60                  65 agc tgg gac cag cag ctg aac ctg gcc tac gtg ggc gcc gtg ccc cac     1496
Ser Trp Asp Gln Gln Leu Asn Leu Ala Tyr Val Gly Ala Val Pro His
         70                  75                  80 aga ggc atc aaa cag gtg aga acc cac tgg ctg ctg gaa ctg gtg aca     1544
Arg Gly Ile Lys Gln Val Arg Thr His Trp Leu Leu Glu Leu Val Thr
         85                  90                  95 acc cgg ggc tcc acc ggc aga ggc ctg agc tac aac ttc acc cac ctg     1592
Thr Arg Gly Ser Thr Gly Arg Gly Leu Ser Tyr Asn Phe Thr His Leu
        100                 105                 110 gac ggc tac ctg gac ctg ctg aga gag aac cag ctg ctg ccc ggc ttc     1640
Asp Gly Tyr Leu Asp Leu Leu Arg Glu Asn Gln Leu Leu Pro Gly Phe
115                 120                 125                 130 gag ctg atg ggc agc gcc agc ggc cac ttc acc gac ttc gag gac aag     1688
Glu Leu Met Gly Ser Ala Ser Gly His Phe Thr Asp Phe Glu Asp Lys
                135                 140                 145 cag caa gtc ttt gag tgg aag gac ctg gtg tcc agc ctg gcc aga cgg     1736
Gln Gln Val Phe Glu Trp Lys Asp Leu Val Ser Ser Leu Ala Arg Arg
                150                 155                 160 tac atc ggc aga tac gga ctg gcc cac gtg tcc aag tgg aac ttc gag     1784
Tyr Ile Gly Arg Tyr Gly Leu Ala His Val Ser Lys Trp Asn Phe Glu
        165                 170                 175 aca tgg aac gag ccc gac cac cac gac ttc gac aac gtg tca atg acc     1832
Thr Trp Asn Glu Pro Asp His His Asp Phe Asp Asn Val Ser Met Thr
        180                 185                 190 atg cag ggc ttt ctg aac tac tac gac gcc tgc tcc gag ggc ctg aga     1880
Met Gln Gly Phe Leu Asn Tyr Tyr Asp Ala Cys Ser Glu Gly Leu Arg
195                 200                 205                 210 gcc gcc agt cct gcc ctg aga ctg gga ccc ggc gat agc ttc cac         1928
Ala Ala Ser Pro Ala Leu Arg Leu Gly Pro Gly Asp Ser Phe His
                215                 220                 225 acc ccc ccc aga agc ccc ctg agc tgg ggc ctg ctg aga cac tgc cac     1976
Thr Pro Pro Arg Ser Pro Leu Ser Trp Gly Leu Leu Arg His Cys His
                230                 235                 240 gac ggc acc aat ttc ttc acc ggc gag gcc ggc gtg cgg ctg gac tac     2024
Asp Gly Thr Asn Phe Phe Thr Gly Glu Ala Gly Val Arg Leu Asp Tyr
```

-continued

```
                245                 250                 255
atc agc ctg cac cgg aag ggc gcc aga agc agc atc agc atc ctg gaa      2072
Ile Ser Leu His Arg Lys Gly Ala Arg Ser Ser Ile Ser Ile Leu Glu
    260                 265                 270 cag gaa aag gtc gtc gcc cag cag atc cgg cag ctg ttc ccc aag ttc      2120
Gln Glu Lys Val Val Ala Gln Gln Ile Arg Gln Leu Phe Pro Lys Phe
275                 280                 285                 290 gcc gac acc ccc atc tac aac gac gag gcc gac ccc ctg gtg gga tgg      2168
Ala Asp Thr Pro Ile Tyr Asn Asp Glu Ala Asp Pro Leu Val Gly Trp
                295                 300                 305 tca ctg cct cag cct tgg aga gcc gac gtg acc tac gcc gct atg gtg      2216
Ser Leu Pro Gln Pro Trp Arg Ala Asp Val Thr Tyr Ala Ala Met Val
            310                 315                 320 gtg aaa gtg atc gcc cag cat cag aac ctg ctg ctg gcc aac acc acc      2264
Val Lys Val Ile Ala Gln His Gln Asn Leu Leu Leu Ala Asn Thr Thr
        325                 330                 335 agc gcc ttc cct tac gcc ctg ctg agc aac gac aac gcc ttc ctg agc      2312
Ser Ala Phe Pro Tyr Ala Leu Leu Ser Asn Asp Asn Ala Phe Leu Ser
    340                 345                 350 tac cac ccc cac ccc ttc gcc cag aga acc ctg acc gcc cgg ttc cag      2360
Tyr His Pro His Pro Phe Ala Gln Arg Thr Leu Thr Ala Arg Phe Gln
355                 360                 365                 370 gtg aac aac acc aga ccc ccc cac gtg cag ctg ctg aga aag ccc gtg      2408
Val Asn Asn Thr Arg Pro Pro His Val Gln Leu Leu Arg Lys Pro Val
                375                 380                 385 ctg acc gct atg gga ctg ctg gct ctg ctg gac gag gaa cag ctg tgg      2456
Leu Thr Ala Met Gly Leu Leu Ala Leu Leu Asp Glu Glu Gln Leu Trp
            390                 395                 400 gcc gaa gtg tcc cag gcc ggc acc gtg ctg gac agc aat cat aca gtg      2504
Ala Glu Val Ser Gln Ala Gly Thr Val Leu Asp Ser Asn His Thr Val
        405                 410                 415 ggc gtg ctg gcc tcc gcc cac aga cct cag gga ccc gcc gat gct tgg      2552
Gly Val Leu Ala Ser Ala His Arg Pro Gln Gly Pro Ala Asp Ala Trp
    420                 425                 430 cgg gct gcc gtg ctg atc tac gcc agc gac gat acc aga gcc cac ccc      2600
Arg Ala Ala Val Leu Ile Tyr Ala Ser Asp Asp Thr Arg Ala His Pro
435                 440                 445                 450 aac aga tcc gtg gcc gtg acc ctg cgg ctg aga ggc gtg cca cca ggc      2648
Asn Arg Ser Val Ala Val Thr Leu Arg Leu Arg Gly Val Pro Pro Gly
                455                 460                 465 cct gga ctg gtg tac gtg acc aga tac ctg gac aac ggc ctg tgc agc      2696
Pro Gly Leu Val Tyr Val Thr Arg Tyr Leu Asp Asn Gly Leu Cys Ser
            470                 475                 480 ccc gac ggc gaa tgg cgc aga ctg ggc aga cct gtg ttc ccc acc gcc      2744
Pro Asp Gly Glu Trp Arg Arg Leu Gly Arg Pro Val Phe Pro Thr Ala
        485                 490                 495 gag cag ttc cgg cgg atg aga gcc gct gag gat cct gtg gct gct gcc      2792
Glu Gln Phe Arg Arg Met Arg Ala Ala Glu Asp Pro Val Ala Ala Ala
    500                 505                 510 cct aga cct ctg cct gct ggc ggc aga ctg acc ctg agg ccc gct ctg      2840
Pro Arg Pro Leu Pro Ala Gly Gly Arg Leu Thr Leu Arg Pro Ala Leu
515                 520                 525                 530 aga ctg cct agt ctg ctg ctg gtg cac gtg tgc gcc agg ccc gag aag      2888
Arg Leu Pro Ser Leu Leu Leu Val His Val Cys Ala Arg Pro Glu Lys
                535                 540                 545 cct ccc ggc cag gtg aca aga ctg aga gcc ctg ccc ctg acc cag ggc      2936
Pro Pro Gly Gln Val Thr Arg Leu Arg Ala Leu Pro Leu Thr Gln Gly
            550                 555                 560 cag ctg gtg ctg gtg tgg tcc gat gag cac gtg ggc agc aag tgc ctg      2984
Gln Leu Val Leu Val Trp Ser Asp Glu His Val Gly Ser Lys Cys Leu
```

```
Gln Leu Val Leu Val Trp Ser Asp Glu His Val Gly Ser Lys Cys Leu
            565                 570                 575 tgg acc tac gag atc cag ttc agc cag gac ggc aag gcc tac acc ccc      3032
Trp Thr Tyr Glu Ile Gln Phe Ser Gln Asp Gly Lys Ala Tyr Thr Pro
        580                 585                 590 gtg tcc cgg aag ccc agc acc ttc aac ctg ttc gtg ttc agc ccc gat      3080
Val Ser Arg Lys Pro Ser Thr Phe Asn Leu Phe Val Phe Ser Pro Asp
595                 600                 605                 610 aca ggc gcc gtg tcc ggc tct tat aga gtg cgg gcc ctg gac tac tgg      3128
Thr Gly Ala Val Ser Gly Ser Tyr Arg Val Arg Ala Leu Asp Tyr Trp
                615                 620                 625 gcc aga ccc ggc cct ttc agc gac ccc gtg ccc tac ctg gaa gtg ccc      3176
Ala Arg Pro Gly Pro Phe Ser Asp Pro Val Pro Tyr Leu Glu Val Pro
            630                 635                 640 gtg cct aga ggc ccc cct agc ccc ggc aac cct tga gtcgacccgg           3222
Val Pro Arg Gly Pro Pro Ser Pro Gly Asn Pro
            645                 650
```

```
gcggcctcga ggacggggtg aactacgcct gaggatccga tcttttttccc tctgccaaaa   3282
attatgggga catcatgaag ccccttgagc atctgacttc tggctaataa aggaaattta   3342
ttttcattgc aatagtgtgt tggaattttt tgtgtctctc actcggaagc aattcgttga   3402
tctgaatttc gaccacccat aatacccatt accctggtag ataagtagca tggcgggtta   3462
atcattaact acaaggaacc cctagtgatg gagttggcca ctccctctct gcgcgctcgc   3522
tcgctcactg aggccgggcg accaaaggtc gcccgacgcc cgggctttgc ccgggcggcc   3582
tcagtgagcg agcgagcgcg cagccttaat taacctaatt cactggccgt cgttttacaa   3642
cgtcgtgact gggaaaaccc tggcgttacc caacttaatc gccttgcagc acatccccct   3702
ttcgccagct ggcgtaatag cgaagaggcc cgcaccgatc gcccttccca acagttgcgc   3762
agcctgaatg gcgaatggga cgcgccctgt agcggcgcat taagcgcggc gggtgtggtg   3822
gttacgcgca gcgtgaccgc tacacttgcc agcgccctag cgcccgctcc tttcgctttc   3882
ttcccttcct ttctcgccac gttcgccggc tttccccgtc aagctctaaa tcgggggctc   3942
cctttagggt tccgatttag tgctttacgg cacctcgacc ccaaaaaact tgattagggt   4002
gatggttcac gtagtgggcc atcgccctga tagacggttt ttcgcccttt gacgttggag   4062
tccacgttct ttaatagtgg actcttgttc caaactggaa caacactcaa ccctatctcg   4122
gtctattctt ttgatttata agggattttg ccgatttcgg cctattggtt aaaaaatgag   4182
ctgatttaac aaaaatttaa cgcgaatttt aacaaaatca tgtgagcaaa aggccagcaa   4242
aaggccagga accgtaaaaa ggccgcgttg ctggcgtttt tccataggct ccgcccccct   4302
gacgagcatc acaaaaatcg acgctcaagt cagaggtggc gaaacccgac aggactataa   4362
agataccagg cgtttccccc tggaagctcc ctcgtgcgct ctcctgttcc gaccctgccg   4422
cttaccggat acctgtccgc ctttctccct tcgggaagcg tggcgctttc tcatagctca   4482
cgctgtaggt atctcagttc ggtgtaggtc gttcgctcca agctgggctg tgtgcacgaa   4542
ccccccgttc agcccgaccg ctgcgcctta tccggtaact atcgtcttga gtccaacccg   4602
gtaagacacg acttatcgcc actggcagca gccactggta acaggattag cagagcgagg   4662
tatgtaggcg gtgctacaga gttcttgaag tggtggccta actacggcta cactagaaga   4722
acagtatttg gtatctgcgc tctgctgaag ccagttacct tcggaaaaag agttggtagc   4782
tcttgatccg gcaaacaaac caccgctggt agcggtggtt tttttgtttg caagcagcag   4842
attacgcgca gaaaaaaagg atctcaagaa gatcctttga tcttttctac ggggtctgac   4902
```

| | |
|---|---|
| gctcagtgga acgaaaactc acgttaaggg attttggtca tgagattatc aaaaaggatc | 4962 |
| ttcacctaga tccttttgat cctccggcgt tcagcctgtg ccacagccga caggatggtg | 5022 |
| accaccattt gccccatatc accgtcggta ctgatcccgt cgtcaataaa ccgaaccgct | 5082 |
| acaccctgag catcaaactc ttttatcagt tggatcatgt cggcggtgtc gcggccaaga | 5142 |
| cggtcgagct tcttcaccag aatgacatca ccttcctcca ccttcatcct cagcaaatcc | 5202 |
| agcccttccc gatctgttga actgccggat gccttgtcgg taaagatgcg gttagctttt | 5262 |
| accccctgcat ctttgagcgc tgaggtctgc ctcgtgaaga aggtgttgct gactcatacc | 5322 |
| aggcctgaat cgccccatca tccagccaga aagtgaggga gccacggttg atgagagctt | 5382 |
| tgttgtaggt ggaccagttg gtgattttga acttttgctt tgccacggaa cggtctgcgt | 5442 |
| tgtcgggaag atgcgtgatc tgatccttca actcagcaaa agttcgattt attcaacaaa | 5502 |
| gccgccgtcc cgtcaagtca gcgtaatgct ctgccagtgt tacaaccaat taaccaattc | 5562 |
| tgattagaaa aactcatcga gcatcaaatg aaactgcaat ttattcatat caggattatc | 5622 |
| aataccatat ttttgaaaaa gccgtttctg taatgaagga gaaaactcac cgaggcagtt | 5682 |
| ccataggatg gcaagatcct ggtatcggtc tgcgattccg actcgtccaa catcaataca | 5742 |
| acctattaat ttcccctcgt caaaaataag gttatcaagt gagaaatcac catgagtgac | 5802 |
| gactgaatcc ggtgagaatg gcaaaagctt atgcatttct ttccagactt gttcaacagg | 5862 |
| ccagccatta cgctcgtcat caaaatcact cgcatcaacc aaaccgttat tcattcgtga | 5922 |
| ttgcgcctga gcgagacgaa atacgcgatc gctgttaaaa ggacaattac aaacaggaat | 5982 |
| cgaatgcaac cggcgcagga acactgccag cgcatcaaca atattttcac ctgaatcagg | 6042 |
| atattcttct aatacctgga atgctgtttt cccggggatc gcagtggtga gtaaccatgc | 6102 |
| atcatcagga gtacggataa aatgcttgat ggtcggaaga ggcataaatt ccgtcagcca | 6162 |
| gtttagtctg accatctcat ctgtaacatc attggcaacg ctacctttgc catgtttcag | 6222 |
| aaacaactct ggcgcatcgg gcttcccata caatcgatag attgtcgcac ctgattgccc | 6282 |
| gacattatcg cgagcccatt tatacccata taaatcagca tccatgttgg aatttaatcg | 6342 |
| cggcctcgag caagacgttt cccgttgaat atggctcata caccccttg tattactgtt | 6402 |
| tatgtaagca gacagtttta ttgttcatga tgatatattt ttatcttgtg caatgtaaca | 6462 |
| tcagagattt tgagacacca tgttctttcc tgcgttatcc cctgattctg tggataaccg | 6522 |
| tattaccgcc tttgagtgag ctgataccgc tcgccgcagc cgaacgaccg agcgcagcga | 6582 |
| gtcagtgagc gaggaagcgg aagagcgccc aatacgcaaa ccgcctctcc ccgcgcgttg | 6642 |
| gccgattcat taatgcagct ggcacgacag gtttcccgac tggaaagcgg gcagtgagcg | 6702 |
| caacgcaatt aatgtgagtt agctcactca ttaggcaccc caggctttac actttatgct | 6762 |
| tccggctcgt atgttgtgtg gaattgtgag cggataacaa tttcacacag gaaacagcta | 6822 |
| tgaccatgat tacgccagat ttaattaagg ccttaattag g | 6863 |

<210> SEQ ID NO 4
<211> LENGTH: 653
<212> TYPE: PRT
<213> ORGANISM: Artificial sequence
<220> FEATURE:
<223> OTHER INFORMATION: Synthetic Construct

<400> SEQUENCE: 4

```
Met Arg Pro Leu Arg Pro Arg Ala Ala Leu Leu Ala Leu Leu Ala Ser
1               5                   10                  15
```

```
Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Arg Gly Leu Ser Tyr Asn Phe Thr
                100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
```

```
            435                 440                 445
His Pro Asn Arg Ser Val Ala Val Thr Leu Arg Leu Arg Gly Val Pro
        450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

```
<210> SEQ ID NO 5
<211> LENGTH: 20
<212> TYPE: DNA
<213> ORGANISM: Artificial sequence
<220> FEATURE:
<223> OTHER INFORMATION: Synthetic (forward primer)

<400> SEQUENCE: 5
gccaaaaatt atggggacat                                             20

<210> SEQ ID NO 6
<211> LENGTH: 27
<212> TYPE: DNA
<213> ORGANISM: Artificial sequence
<220> FEATURE:
<223> OTHER INFORMATION: synthetic (probe)

<400> SEQUENCE: 6
atgaagcccc ttgagcatct gacttct                                     27

<210> SEQ ID NO 7
<211> LENGTH: 653
<212> TYPE: PRT
<213> ORGANISM: Artificial sequence
<220> FEATURE:
<223> OTHER INFORMATION: synthetic hIDUA variant

<400> SEQUENCE: 7

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
```

```
            20                  25                  30
Gln Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
 65                  70                  75                  80

Pro His Arg Gly Ile Lys Gln Val Arg Thr His Trp Leu Leu Glu Leu
                 85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
            130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
                180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
    210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
            435                 440                 445
```

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 8
<211> LENGTH: 653
<212> TYPE: PRT
<213> ORGANISM: Artificial sequence
<220> FEATURE:
<223> OTHER INFORMATION: Synthetic hIDUA variant 020976

<400> SEQUENCE: 8

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro Gln Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
    130                 135                 140

Asp Lys Gln Gln Val Phe Glu Trp Lys Asp Leu Val Ser Ser Leu Ala
145                 150                 155                 160

```
Arg Arg Tyr Ile Gly Arg Tyr Gly Leu Ala His Val Ser Lys Trp Asn
            165                 170                 175

Phe Glu Thr Trp Asn Glu Pro Asp His His Asp Phe Asp Asn Val Ser
        180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
        210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
            245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
        290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
            325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
        370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
            405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
            435                 440                 445

His Pro Asn Arg Ser Val Ala Val Thr Leu Arg Leu Arg Gly Val Pro
        450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
            485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
        530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
            565                 570                 575
```

-continued

```
Cys Leu Trp Thr Tyr Glu Ile Gln Phe Ser Gln Asp Gly Lys Ala Tyr
                580                 585                 590
Thr Pro Val Ser Arg Lys Pro Ser Thr Phe Asn Leu Phe Val Phe Ser
            595                 600                 605
Pro Asp Thr Gly Ala Val Ser Gly Ser Tyr Arg Val Arg Ala Leu Asp
        610                 615                 620
Tyr Trp Ala Arg Pro Gly Pro Phe Ser Asp Pro Val Pro Tyr Leu Glu
625                 630                 635                 640
Val Pro Val Pro Arg Gly Pro Ser Pro Gly Asn Pro
            645                 650

<210> SEQ ID NO 9
<211> LENGTH: 653
<212> TYPE: PRT
<213> ORGANISM: Artificial sequence
<220> FEATURE:
<223> OTHER INFORMATION: Synthetic (hIDUA variant 003356)

<400> SEQUENCE: 9

Met Arg Pro Leu Arg Pro Arg Ala Ala Leu Leu Ala Leu Leu Ala Ser
1               5                   10                  15
Leu Leu Ala Ala Pro Pro Val Ala Pro Ala Glu Ala Pro His Leu Val
            20                  25                  30
His Val Asp Ala Ala Arg Ala Leu Trp Pro Leu Arg Arg Phe Trp Arg
        35                  40                  45
Ser Thr Gly Phe Cys Pro Pro Leu Pro His Ser Gln Ala Asp Gln Tyr
    50                  55                  60
Val Leu Ser Trp Asp Gln Gln Leu Asn Leu Ala Tyr Val Gly Ala Val
65                  70                  75                  80
Pro His Arg Gly Ile Lys Gln Val Arg Thr His Trp Leu Leu Glu Leu
                85                  90                  95
Val Thr Thr Arg Gly Ser Thr Gly Gln Gly Leu Ser Tyr Asn Phe Thr
            100                 105                 110
His Leu Asp Gly Tyr Leu Asp Leu Leu Arg Glu Asn Gln Leu Leu Pro
        115                 120                 125
Gly Phe Glu Leu Met Gly Ser Ala Ser Gly His Phe Thr Asp Phe Glu
    130                 135                 140
Asp Lys Gln Gln Val Phe Glu Trp Lys Asp Leu Val Ser Ser Leu Ala
145                 150                 155                 160
Arg Arg Tyr Ile Gly Arg Tyr Gly Leu Ala His Val Ser Lys Trp Asn
                165                 170                 175
Phe Glu Thr Trp Asn Glu Pro Asp His His Asp Phe Asp Asn Val Ser
            180                 185                 190
Met Thr Met Gln Gly Phe Leu Asn Tyr Tyr Asp Ala Cys Ser Glu Gly
        195                 200                 205
Leu Arg Ala Ala Ser Pro Ala Leu Arg Leu Gly Gly Pro Gly Asp Ser
    210                 215                 220
Phe His Thr Pro Pro Arg Ser Pro Leu Ser Trp Gly Leu Leu Arg His
225                 230                 235                 240
Cys His Asp Gly Thr Asn Phe Phe Thr Gly Glu Ala Gly Val Arg Leu
                245                 250                 255
Asp Tyr Ile Ser Leu His Arg Lys Gly Ala Arg Ser Ser Ile Ser Ile
            260                 265                 270
Leu Glu Gln Glu Lys Val Val Ala Gln Gln Ile Arg Gln Leu Phe Pro
        275                 280                 285
```

-continued

```
Lys Phe Ala Asp Thr Pro Ile Tyr Asn Asp Glu Ala Asp Pro Leu Val
            290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

<210> SEQ ID NO 10
<211> LENGTH: 653
<212> TYPE: PRT
<213> ORGANISM: Artificial sequence
<220> FEATURE:
<223> OTHER INFORMATION: Synthetic (hIDUA variant 003367)

<400> SEQUENCE: 10

```
Met Arg Pro Leu Arg Pro Arg Ala Ala Leu Leu Ala Leu Leu Ala Ser
1               5                   10                  15
Leu Leu Ala Ala Pro Pro Val Ala Pro Ala Glu Ala Pro His Leu Val
            20                  25                  30
His Val Asp Ala Ala Arg Ala Leu Trp Pro Leu Arg Arg Phe Trp Arg
            35                  40                  45
Ser Thr Gly Phe Cys Pro Pro Leu Pro His Ser Gln Ala Asp Gln Tyr
        50                  55                  60
Val Leu Ser Trp Asp Gln Gln Leu Asn Leu Ala Tyr Val Gly Ala Val
65                  70                  75                  80
Pro His Arg Gly Ile Lys Gln Val Arg Thr His Trp Leu Leu Glu Leu
                85                  90                  95
Val Thr Thr Arg Gly Ser Thr Gly Arg Gly Leu Ser Tyr Asn Phe Thr
            100                 105                 110
His Leu Asp Arg Tyr Leu Asp Leu Leu Arg Glu Asn Gln Leu Leu Pro
            115                 120                 125
Gly Phe Glu Leu Met Gly Ser Ala Ser Gly His Phe Thr Asp Phe Glu
    130                 135                 140
Asp Lys Gln Gln Val Phe Glu Trp Lys Asp Leu Val Ser Ser Leu Ala
145                 150                 155                 160
Arg Arg Tyr Ile Gly Arg Tyr Gly Leu Ala His Val Ser Lys Trp Asn
                165                 170                 175
Phe Glu Thr Trp Asn Glu Pro Asp His His Asp Phe Asp Asn Val Ser
            180                 185                 190
Met Thr Met Gln Gly Phe Leu Asn Tyr Tyr Asp Ala Cys Ser Glu Gly
            195                 200                 205
Leu Arg Ala Ala Ser Pro Ala Leu Arg Leu Gly Gly Pro Gly Asp Ser
    210                 215                 220
Phe His Thr Pro Pro Arg Ser Pro Leu Ser Trp Gly Leu Leu Arg His
225                 230                 235                 240
Cys His Asp Gly Thr Asn Phe Phe Thr Gly Glu Ala Gly Val Arg Leu
                245                 250                 255
Asp Tyr Ile Ser Leu His Arg Lys Gly Ala Arg Ser Ser Ile Ser Ile
            260                 265                 270
Leu Glu Gln Glu Lys Val Val Ala Gln Gln Ile Arg Gln Leu Phe Pro
    275                 280                 285
Lys Phe Ala Asp Thr Pro Ile Tyr Asn Asp Glu Ala Asp Pro Leu Val
    290                 295                 300
Gly Trp Ser Leu Pro Gln Pro Trp Arg Ala Asp Val Thr Tyr Ala Ala
305                 310                 315                 320
Met Val Val Lys Val Ile Ala Gln His Gln Asn Leu Leu Leu Ala Asn
                325                 330                 335
Thr Thr Ser Ala Phe Pro Tyr Ala Leu Leu Ser Asn Asp Asn Ala Phe
            340                 345                 350
Leu Ser Tyr His Pro His Pro Phe Ala Gln Arg Thr Leu Thr Ala Arg
            355                 360                 365
Phe Gln Val Asn Asn Thr Arg Pro Pro His Val Gln Leu Leu Arg Lys
    370                 375                 380
Pro Val Leu Thr Ala Met Gly Leu Leu Ala Leu Leu Asp Glu Glu Gln
385                 390                 395                 400
Leu Trp Ala Glu Val Ser Gln Ala Gly Thr Val Leu Asp Ser Asn His
                405                 410                 415
Thr Val Gly Val Leu Ala Ser Ala His Arg Pro Gln Gly Pro Ala Asp
```

```
            420                 425                 430
Ala Trp Arg Ala Ala Val Leu Ile Tyr Ala Ser Asp Asp Thr Arg Ala
            435                 440                 445

His Pro Asn Arg Ser Val Ala Val Thr Leu Arg Leu Arg Gly Val Pro
            450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
            485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
            515                 520                 525

Ala Leu Arg Leu Pro Ser Leu Leu Leu Val His Val Cys Ala Arg Pro
            530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
            565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
            595                 600                 605

Pro Asp Thr Gly Ala Val Ser Gly Ser Tyr Arg Val Arg Ala Leu Asp
610                 615                 620

Tyr Trp Ala Arg Pro Gly Pro Phe Ser Asp Pro Val Pro Tyr Leu Glu
625                 630                 635                 640

Val Pro Val Pro Arg Gly Pro Ser Pro Gly Asn Pro
            645                 650

<210> SEQ ID NO 11
<211> LENGTH: 653
<212> TYPE: PRT
<213> ORGANISM: Artificial sequence
<220> FEATURE:
<223> OTHER INFORMATION: Synthetic (hIDUA variant 003359)

<400> SEQUENCE: 11

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
            50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
            85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
```

```
                130             135             140
Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
                195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
                260                 265                 270

Leu Glu Gln Glu Lys Val Ala Ala Gln Gln Ile Arg Gln Leu Phe Pro
                275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
                340                 345                 350

Leu Ser Tyr His Pro His Pro Phe Ala Gln Arg Thr Leu Thr Ala Arg
                355                 360                 365

Phe Gln Val Asn Asn Thr Arg Pro Pro His Val Gln Leu Leu Arg Lys
                370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
                420                 425                 430

Ala Trp Arg Ala Ala Val Leu Ile Tyr Ala Ser Asp Asp Thr Arg Ala
                435                 440                 445

His Pro Asn Arg Ser Val Ala Val Thr Leu Arg Leu Arg Gly Val Pro
450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
                500                 505                 510

Ala Ala Pro Arg Pro Leu Pro Ala Gly Gly Arg Leu Thr Leu Arg Pro
                515                 520                 525

Ala Leu Arg Leu Pro Ser Leu Leu Leu Val His Val Cys Ala Arg Pro
                530                 535                 540

Glu Lys Pro Pro Gly Gln Val Thr Arg Leu Arg Ala Leu Pro Leu Thr
545                 550                 555                 560
```

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
                580                 585                 590

Thr Pro Val Ser Arg Lys Pro Ser Thr Phe Asn Leu Phe Val Phe Ser
                595                 600                 605

Pro Asp Thr Gly Ala Val Ser Gly Ser Tyr Arg Val Arg Ala Leu Asp
                610                 615                 620

Tyr Trp Ala Arg Pro Gly Pro Phe Ser Asp Pro Val Pro Tyr Leu Glu
625                 630                 635                 640

Val Pro Val Pro Arg Gly Pro Ser Pro Gly Asn Pro
                645                 650

<210> SEQ ID NO 12
<211> LENGTH: 653
<212> TYPE: PRT
<213> ORGANISM: Artificial sequence
<220> FEATURE:
<223> OTHER INFORMATION: Synthetic sequence (hIDAU variant 017436)

<400> SEQUENCE: 12

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
                20                  25                  30

His Val Asp Ala Ala Arg Ala Leu Trp Pro Leu Arg Arg Phe Trp Arg
                35                  40                  45

Ser Thr Gly Phe Cys Pro Pro Leu Pro His Ser Gln Ala Asp Gln Tyr
            50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
                100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
                180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
        210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
                260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
    290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Ala Asn
                325                 330                 335

Thr Thr Ser Ala Phe Pro Tyr Ala Leu Arg Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
    370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
    515                 520                 525

Ala Leu Arg Leu Pro Ser Leu Leu Val His Val Cys Ala Arg Pro
530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
    595                 600                 605

Pro Asp Thr Gly Ala Val Ser Gly Ser Tyr Arg Val Arg Ala Leu Asp
610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 13
<211> LENGTH: 653
<212> TYPE: PRT
<213> ORGANISM: Artificial sequence
<220> FEATURE:

<223> OTHER INFORMATION: synthetic sequence (hIDUA variant 003364)

<400> SEQUENCE: 13

```
Met Arg Pro Leu Arg Pro Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Thr Gln Arg Thr Leu Thr Ala Arg
        355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400
```

```
Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Val Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 14
<211> LENGTH: 653
<212> TYPE: PRT
<213> ORGANISM: Artificial sequence
<220> FEATURE:
<223> OTHER INFORMATION: Synthetic (hIDUA variant 066228)

<400> SEQUENCE: 14

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110
```

```
His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
            290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
            435                 440                 445

Asn Pro Asn Arg Ser Val Ala Val Thr Leu Arg Leu Arg Gly Val Pro
450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
            515                 520                 525

Ala Leu Arg Leu Pro Ser Leu Leu Leu Val His Val Cys Ala Arg Pro
```

```
                530                 535                 540
Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
                580                 585                 590

Thr Pro Val Ser Arg Lys Pro Ser Thr Phe Asn Leu Phe Val Phe Ser
                595                 600                 605

Pro Asp Thr Gly Ala Val Ser Gly Ser Tyr Arg Val Arg Ala Leu Asp
                610                 615                 620

Tyr Trp Ala Arg Pro Gly Pro Phe Ser Asp Pro Val Pro Tyr Leu Glu
625                 630                 635                 640

Val Pro Val Pro Arg Gly Pro Ser Pro Gly Asn Pro
                645                 650

<210> SEQ ID NO 15
<211> LENGTH: 653
<212> TYPE: PRT
<213> ORGANISM: Artificial sequence
<220> FEATURE:
<223> OTHER INFORMATION: synthetic sequence (hIDUA 003372)

<400> SEQUENCE: 15

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
                20                  25                  30

His Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
                100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
                180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
        210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
```

```
                    245                 250                 255
Asp Tyr Ile Ser Leu His Arg Lys Gly Ala Arg Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
        290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
                355                 360                 365

Phe Gln Val Asn Asn Thr Arg Pro Pro His Val Gln Leu Leu Arg Lys
        370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
        435                 440                 445

His Pro Asn Arg Ser Ile Ala Val Thr Leu Arg Leu Arg Gly Val Pro
    450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650

<210> SEQ ID NO 16
```

<211> LENGTH: 653
<212> TYPE: PRT
<213> ORGANISM: Artificial sequence
<220> FEATURE:
<223> OTHER INFORMATION: Synthetic sequence (hIDUA variant 0066231)

<400> SEQUENCE: 16

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
        115                 120                 125

Gly Phe Glu Leu Met Gly Ser Ala Ser Gly His Phe Thr Asp Phe Glu
130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
        195                 200                 205

Leu Arg Ala Ala Ser Pro Ala Leu Arg Leu Gly Gly Pro Gly Asp Ser
210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
        275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
        355                 360                 365

Phe Gln Val Asn Asn Thr Arg Pro Pro His Val Gln Leu Leu Arg Lys
370                 375                 380
```

-continued

```
Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
            405                 410                 415

Thr Val Gly Val Leu Ala Ser Ala His Arg Pro Gln Gly Pro Ala Asp
        420                 425                 430

Ala Trp Arg Ala Ala Val Leu Ile Tyr Ala Ser Asp Asp Thr Arg Ala
    435                 440                 445

His Pro Asn Arg Ser Val Ala Val Thr Leu Arg Leu Arg Gly Val Pro
450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
            485                 490                 495

Thr Ala Glu Gln Phe Arg Arg Met Arg Ala Ala Glu Asp Pro Val Ala
        500                 505                 510

Ala Ala Pro Arg Pro Leu Pro Ala Gly Gly Arg Leu Thr Leu Arg Pro
    515                 520                 525

Ala Leu Arg Leu Pro Ser Leu Leu Leu Val His Val Cys Ala Arg Pro
530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
            565                 570                 575

Cys Leu Trp Thr Tyr Glu Ile Gln Phe Ser Gln Asp Gly Lys Thr Tyr
        580                 585                 590

Thr Pro Val Ser Arg Lys Pro Ser Thr Phe Asn Leu Phe Val Phe Ser
    595                 600                 605

Pro Asp Thr Gly Ala Val Ser Gly Ser Tyr Arg Val Arg Ala Leu Asp
610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
            645                 650
```

<210> SEQ ID NO 17
<211> LENGTH: 653
<212> TYPE: PRT
<213> ORGANISM: Artificial sequence
<220> FEATURE:
<223> OTHER INFORMATION: Synthetic (hIDUA variant A622T)

<400> SEQUENCE: 17

```
Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

His Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80

Pro His Arg Gly Ile Lys Gln Val Arg Thr His Trp Leu Leu Glu Leu
            85                  90                  95
```

```
Val Thr Thr Arg Gly Ser Thr Gly Arg Gly Leu Ser Tyr Asn Phe Thr
            100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
            130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
            180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
            210                 215                 220

Phe His Thr Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
            260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
            340                 345                 350

Leu Ser Tyr His Pro His Pro Phe Ala Gln Arg Thr Leu Thr Ala Arg
            355                 360                 365

Phe Gln Val Asn Asn Thr Arg Pro Pro His Val Gln Leu Leu Arg Lys
370                 375                 380

Pro Val Leu Thr Ala Met Gly Leu Leu Ala Leu Leu Asp Glu Glu Gln
385                 390                 395                 400

Leu Trp Ala Glu Val Ser Gln Ala Gly Thr Val Leu Asp Ser Asn His
                405                 410                 415

Thr Val Gly Val Leu Ala Ser Ala His Arg Pro Gln Gly Pro Ala Asp
            420                 425                 430

Ala Trp Arg Ala Ala Val Leu Ile Tyr Ala Ser Asp Asp Thr Arg Ala
            435                 440                 445

His Pro Asn Arg Ser Val Ala Val Thr Leu Arg Leu Arg Gly Val Pro
            450                 455                 460

Pro Gly Pro Gly Leu Val Tyr Val Thr Arg Tyr Leu Asp Asn Gly Leu
465                 470                 475                 480

Cys Ser Pro Asp Gly Glu Trp Arg Arg Leu Gly Arg Pro Val Phe Pro
                485                 490                 495

Thr Ala Glu Gln Phe Arg Arg Met Arg Ala Ala Glu Asp Pro Val Ala
            500                 505                 510
```

```
Ala Ala Pro Arg Pro Leu Pro Ala Gly Gly Arg Leu Thr Leu Arg Pro
        515             520                 525

Ala Leu Arg Leu Pro Ser Leu Leu Leu Val His Val Cys Ala Arg Pro
        530             535                 540

Glu Lys Pro Pro Gly Gln Val Thr Arg Leu Arg Ala Leu Pro Leu Thr
545             550                 555                 560

Gln Gly Gln Leu Val Leu Val Trp Ser Asp Glu His Val Gly Ser Lys
            565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595             600                 605

Pro Asp Thr Gly Ala Val Ser Gly Ser Tyr Arg Val Arg Thr Leu Asp
        610             615                 620

Tyr Trp Ala Arg Pro Gly Pro Phe Ser Asp Pro Val Pro Tyr Leu Glu
625             630                 635                 640

Val Pro Val Pro Arg Gly Pro Pro Ser Pro Gly Asn Pro
                645             650
```